United States Patent
Ben et al.

(10) Patent No.: US 11,207,347 B2
(45) Date of Patent: Dec. 28, 2021

(54) STABILIZED AMORPHOUS CALCIUM CARBONATE FOR TREATMENT OF NEUROLOGICAL, MUSCULAR AND INFERTILITY DISEASES OR CONDITIONS

(71) Applicant: AMORPHICAL LTD., Ness Ziona (IL)

(72) Inventors: Yosef Ben, Arava (IL); Abraham Shahar, Rehovot (IL); Amir Arav, Tel Aviv (IL)

(73) Assignee: AMORPHICAL LTD., Ness Ziona (IL)

( * ) Notice: Subject to any disclaimer, the term of this patent is extended or adjusted under 35 U.S.C. 154(b) by 0 days.

(21) Appl. No.: 16/934,689

(22) Filed: Jul. 21, 2020

(65) Prior Publication Data

US 2020/0345764 A1   Nov. 5, 2020

Related U.S. Application Data

(62) Division of application No. 16/069,762, filed as application No. PCT/IL2017/050059 on Jan. 17, 2017, now Pat. No. 10,758,566.

(60) Provisional application No. 62/279,843, filed on Jan. 18, 2016, provisional application No. 62/279,844, filed on Jan. 18, 2016, provisional application No. 62/279,845, filed on Jan. 18, 2016, provisional application No. 62/376,428, filed on Aug. 18, 2016.

(51) Int. Cl.

| | |
|---|---|
| *A61K 33/10* | (2006.01) |
| *A61K 9/00* | (2006.01) |
| *A61K 9/06* | (2006.01) |
| *A61K 9/10* | (2006.01) |
| *A61P 21/00* | (2006.01) |
| *A61P 15/08* | (2006.01) |
| *A61K 47/02* | (2006.01) |
| *A61K 47/12* | (2006.01) |
| *A61K 47/24* | (2006.01) |
| *A61K 47/26* | (2006.01) |
| *C12N 5/073* | (2010.01) |
| *C12N 5/076* | (2010.01) |
| *C12N 5/071* | (2010.01) |

(52) U.S. Cl.
CPC ............ *A61K 33/10* (2013.01); *A61K 9/0019* (2013.01); *A61K 9/0053* (2013.01); *A61K 9/0095* (2013.01); *A61K 9/06* (2013.01); *A61K 9/10* (2013.01); *A61K 47/02* (2013.01); *A61K 47/12* (2013.01); *A61K 47/24* (2013.01); *A61K 47/26* (2013.01); *A61P 15/08* (2018.01); *A61P 21/00* (2018.01); *C12N 5/061* (2013.01); *C12N 5/0604* (2013.01); *C12N 5/0612* (2013.01); *C12N 2500/14* (2013.01)

(58) Field of Classification Search
CPC .............................. A61K 31/10; A61P 21/00
See application file for complete search history.

(56) References Cited

U.S. PATENT DOCUMENTS 4,757,017 A   7/1988   Cheung

FOREIGN PATENT DOCUMENTS

| WO | 2005/115414 A2 | 12/2005 |
|---|---|---|
| WO | 2008/041236 A2 | 4/2008 |
| WO | 2009/053967 A1 | 4/2009 |
| WO | 2013/088440 A1 | 6/2013 |
| WO | 2014/024191 A1 | 2/2014 |
| WO | 2014/122658 A1 | 8/2014 |
| WO | 2016/016893 A1 | 2/2016 |
| WO | 2016/016895 A1 | 2/2016 |
| WO | 2016/193982 A1 | 12/2016 |
| WO | 2016193983 A1 | 12/2016 |
| WO | 2017/125917 A1 | 7/2017 |

OTHER PUBLICATIONS

Agarwal and Sekhon (2010) The role of antioxidant therapy in the treatment of male infertility. Hum Fertil (Camb) 13(4): 217-225.
Amann and Waberski (2014) Computer-assisted sperm analysis (CASA): capabilities and potential developments. Theriogenology 81(1): 5-17.
Bentov et al., (2010) Stabilization of amorphous calcium carbonate by phosphate rich organic matrix proteins and by single phosphoamino acids. J Struct Biol 171(2): 207-215.
Bhoumik et al., (2014) Optimum calcium concentration: a crucial factor in regulating sperm motility in vitro. Cell Biochem Biophys 70(2): 1177-1183.
Boland et al., (1996) Skeletal, cardiac, and smooth muscle failure in Duchenne muscular dystrophy. Pediatr Neurol 14(1): 7-12, abstract.
Bursac et al., (2015) Synergizing Engineering and Biology to Treat and Model Skeletal Muscle Injury and Disease. Annu Rev Biomed Eng 17: 217-242.
Culligan and Ohlendieck (2002) Abnormal Calcium Handling in Muscular Dystrophy. Basic Appl Myol 12(4): 147-157.
Datta et al., (2015) Add-ons in IVF programme—Hype or Hope? Facts Views Vis Obgyn 7(4): 241-250.
Joyce et al., (2012) Bone health and associated metabolic complications in neuromuscular diseases. Phys Med Rehabil Clin N Am 23(4): 773-799.
Kevenaar and Hoogenraad (2015) The axonal cytoskeleton: from organization to function. Front Mol Neurosci 8: 44; 12 pages.
Kumar and Singh (2015) Trends of male factor infertility, an important cause of infertility: A review of literature. J Hum Reprod Sci 8(4): 191-196.

(Continued)

*Primary Examiner* — Kevin E Weddington

(74) *Attorney, Agent, or Firm* — Marcus S. Simon

(57) ABSTRACT

Stabilized amorphous calcium carbonate (ACC) for treatment of several neurological, muscular and infertility diseases and conditions is provided. In particular, the stabilized ACC may be used in the treatment of axonal defects and muscular dystrophy. In addition, provided are improved methods used in assistant reproductive technology. Examples of such methods are in vitro fertilization and improvement of sperm quality. The improved IVF method, for example, comprises addition of the stabilized ACC to the cell culture medium in which the stages of fertilization and embryo development occurs.

5 Claims, 11 Drawing Sheets

(56) References Cited

OTHER PUBLICATIONS

Meiron et al., (2011) Solubility and bioavailability of stabilized amorphous calcium carbonate. J Bone Miner Res 26(2): 364-372.

Nasiri and Eftekhari-Yazdi (2015) An overview of the available methods for morphological scoring of pre-implantation embryos in in vitro fertilization. Cell J 16(4): 392-405.

Rahman et al., (2014) Calcium Influx and Male Fertility in the Context of the Sperm Proteome: An Update. BioMed Research International 2014: 841615; 13 pages.

Shaltiel et al., (2013) Bone loss prevention in ovariectomized rats using stable amorphous calcium carbonate. Health 5(7A2): 18-29.

Shechter et al., (2008) A gastrolith protein serving a dual role in the formation of an amorphous mineral containing extracellular matrix. Proc Natl Acad Sci U S A 105(20): 7129-7134.

Shin et al., (2013) Wasting mechanisms in muscular dystrophy. Int J Biochem Cell Biol 45(10): 2266-2279.

Tolba et al., (2016) High biocompatibility and improved osteogenic potential of amorphous calcium carbonate/vaterite. J Mater Chem B 4: 376-386.

Vaisman et al., (2014) Increased calcium absorption from synthetic stable amorphous calcium carbonate: double-blind randomized crossover clinical trial in postmenopausal women. J Bone Miner Res 29(10): 2203-2209.

DMD_M.2.1.005 (SOP (ID) Number): "The use of four limb hanging tests to monitor muscle strength and condition over time"; George Carlson (Author), Maaike van Putten (Official reviewer). Issued: Aug. 3, 2011 and Last reviewed: Jun. 29, 2016; 11 pages.

"Testing the Effect of Crustacean's Gastrolith Nutraceutical on Mineralization Rate During Distraction Osteogenesis" Amorfical (Collaborator), Ron Lamdan, Hadassah Medical Organization (Responsible Party). Study NCT01087437, last updated Mar. 30, 2014 (v6). Retrieved from https://clinicaltrials.gov/ct2/history/NCT01087437?V_6=View#StudyPageTop on Jan. 24, 2019; 4 pages.

Duchenne Diagnosis of Bone and Joint Disorders. Edited by Resnick D; 4th edition, 2009. Elsevier (Singapore) Pte Ltd.; p. 3595. With machine translation; 3 pages.

Neuronal Synaptic Transmission Cells and Molecular Biology (Neurobiology). Edited by Zuhang S, 2008. Shanghai Science and Technology Press; p. 69. With machine translation; 3 pages.

Pathology. Edited by Enhua W, 2003. Higher Education Press, Beijing, China; p. 307. With machine translation; 4 pages.

Stoelting's Anesthesia and Co-Existing Disease. Edited by Hines RL and Marschall K, 2012. Elsevier (Singapore) Pte Ltd.; p. 420. With machine translation; 3 pages.

Merck Manual, 17th Edition, 1999, 3 pages.

Wagner et al., (2007) Current treatment of adult Duchenne muscular dystrophy. Biochim Biophys Acta 1772(2): 229-237.

Brusentsev et al., (2014) Traditional and Modern Approaches to Culture of Preimplantation Mammalian Embryos In Vitro. Russian Journal of Developmental Biology 45(2): 73-88; English abstract on p. 88.

FIG. 12
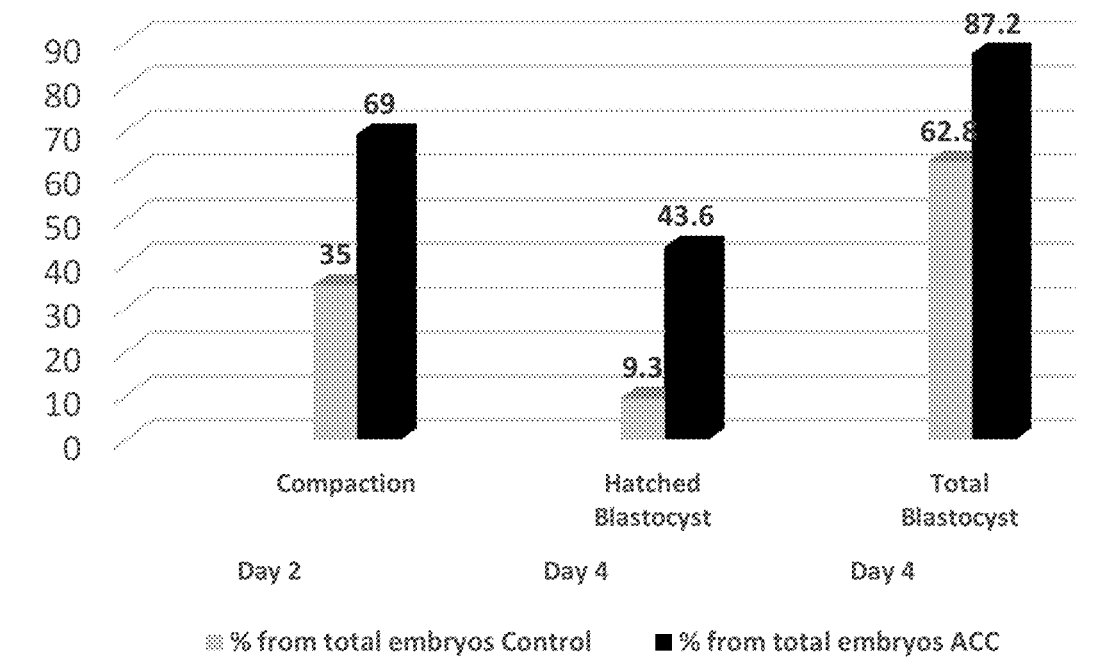
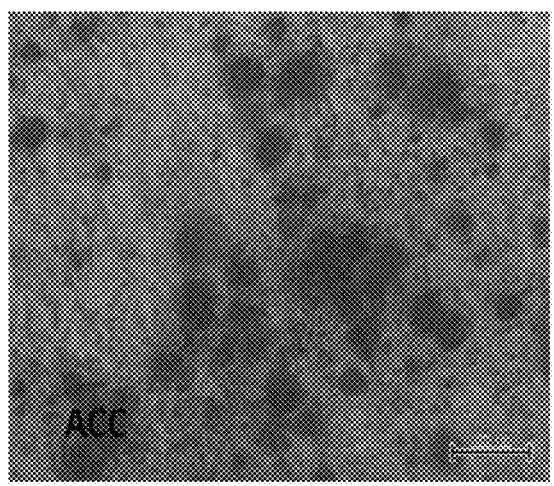
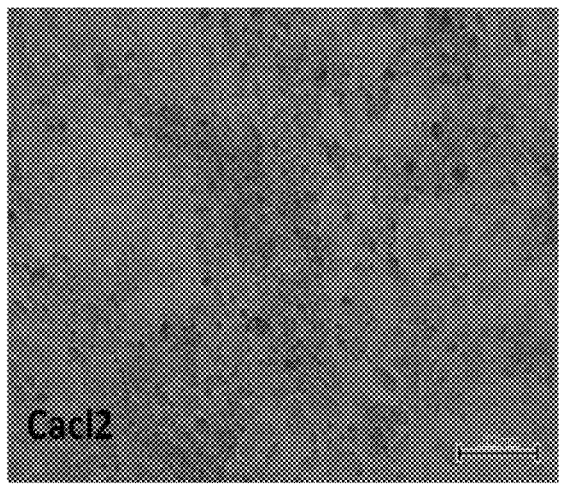
FIG. 13 A  FIG. 13B

STABILIZED AMORPHOUS CALCIUM CARBONATE FOR TREATMENT OF NEUROLOGICAL, MUSCULAR AND INFERTILITY DISEASES OR CONDITIONS

FIELD OF THE INVENTION

The present invention provides stabilized amorphous calcium carbonate (ACC) for treatment of certain muscular, neurological and infertility diseases or conditions. In addition, the stabilized ACC may be used in different assisted reproductive technology e.g. for enhancing the growth of mammal embryos or for improvement of sperm quality.

BACKGROUND OF THE INVENTION

It has been shown in pre-clinical and clinical bioavailability models that administration of ACC resulted in an enhancement of calcium bioavailability (Meiron et al., *J Bone Miner Res.* 2011, 26(2):364-72, Shaltiel et al., Health 5, 2013, 18-29, and Vaisman et al., Journal of Bone and Mineral Research, 2014, 29 (10), pp 2203-2209), an effect which is especially important in relieving calcium malabsorption related conditions and disorders. Oral administration of ACC led to a positive effect on bone parameters, demonstrated by antiresorptive action, anabolic effects and maintenance of bone mechanical strength in an osteoporosis prevention model (Shaltiel et al.). WO 2013/088440 discloses amorphous calcium carbonate compositions for use in treatment of calcium malabsorption and malabsorption associated disorders, diseases and conditions, and for increasing bone mineral density in calcium malabsorption and bone metabolism associated disorders.

WO 2005/115414 describes orally administrable compositions comprising stable ACC as well as method for treating osteoporosis, osteomalacia and related diseases. WO 2008/041236 describes formulations containing amorphous or microcrystalline calcium carbonate which are efficient in treating various pathological conditions including proliferative diseases, neurological disorders and muscoloskeletal disorders. WO 2009/053967 describes compositions containing amorphous calcium carbonate (ACC), and at least one phosphorylated amino acid or phosphorylated peptide. Said compositions may be used for treatment of various diseases listed therein.

Nerve injuries are common in clinical practice. There are many examples where damage of peripheral nerve, caused by accident or the like, is unable to be completely restored. There are also many clinical examples where peripheral nerve must be excised as a result of surgical operations in general. While the central nervous system (CNS) has a long and a weak self-repair of nerve fiber, the peripheral nervous system (PNS) has the ability for nerve repair by rapid nerve fiber regeneration. Studies on the recovery of PNS functionality after injury have become a rapidly growing field dedicated to the searching of suitable ways for facilitate and guide axonal regeneration.

Various approaches have been developed in an attempt to regenerate injured peripheral nerves. One such technique involves the actual suturing of the proximal and distal ends of the severed nerve. The use of various conduits, sutured in between the proximal and distal nerve stumps, for the guidance of the severed regenerated axons has been actively pursued.

Additional diseases that currently lack sufficient treatment relate to a muscular dystrophy. Muscular dystrophy is a group of muscle diseases that weaken the musculoskeletal system and hamper locomotion. Muscular dystrophies are characterized by progressive skeletal muscle weakness, defects in muscle proteins, and the death of muscle cells and tissue. One of such diseases is Duchenne muscular dystrophy (DMD), a lethal muscle wasting disease affecting approximately one in 3500 boys. Duchenne boys have a limited life expectancy of approximately 20 years. The disorder is caused by mutation in the dystrophin gene; many different mutations have been identified as leading to dysfunction of the protein dystrophin. It is characterized by progressive skeletal muscle wasting and degeneration (Shin et al., *Int J Biochem Cell Biol.* 2013, 45(10):2266-79), which also involves abnormal calcium homeostasis. Medical management of the muscular dystrophies has included the use of corticosteroids; however, despite their considerable beneficial effects, prolonged treatment with corticosteroids can lead to osteoporosis. Even without corticosteroids Duchenne muscular dystrophy leads to reduced mobility, which is associated per se with an increased chance of fractures and reduced bone mineral density (Nanette et al., *Phys Med Rehabil Clin N Am.* 2012, 23(4):773-99).

Currently, no satisfactory treatment for DMD or to nerve injury is present nowadays, and reducing the severity of symptoms and improving the quality of life patient suffering from these conditions can be considered as an achievement.

The area of assisted reproductive technology (ART) is aimed at solving the problem of both male and female infertility. One of the main techniques is in vitro fertilization (IVF). The content of the cell culture media may significantly influence the fertilization and embryonic development and thus consequently the outcome of the procedure. The success rate of IVF is mainly related to the number of embryos transferred as well as factors such as embryo quality. Changing the culture media may significantly influence the in vitro embryo development. As elevating the quality of embryos and the number of embryos reached advanced developmental stage may increase the chances for successful conception, finding the optimal conditions for in vitro embryo development can increase the efficiency of the whole IVF process.

"Male factor" infertility is seen as an alteration in sperm concentration and/or motility and/or morphology in at least one sample of two sperm analyzes, collected 1 and 4 weeks apart. In humans, it accounts for 40-50% of infertility and affects approximately 7% of all men. Male infertility is commonly due to deficiencies in the semen or semen quality reflected in low sperm count, motility, and abnormal morphology of sperm (Kumar and Singh, 2015, J. Hum. Reprod. Sci., 8(4): 191-196).

Most techniques of ART, such as Intrauterine Insemination or conventional IVF require at least normal motility of sperm. Several methods for sperm selection are present nowadays, for example a classical washing swim-up technique is used to select the most motile cells based on the natural sperm motility. The selected sperm may be consequently used in the IVF procedure. Numerous techniques for in vitro sperm amelioration were suggested. The results of in vitro experiments suggest that vitamin E may protect spermatozoa from oxidative damage and loss of motility as well as enhance the sperm performance in the hamster egg penetration assay (Agarwal & Sekhon, Human Fertility, December 2010, 13(4): 217-225). Bhoumik et al., (Cell Biochem. Biophys., 2014, 70: 1177-1183) demonstrated that addition of $Ca^{2+}$ ions to calcium-free mediums increases forward sperm motility up to 20%.

The phenomena of male infertility is increasing worldwide (Kumar and Singh) with more and more couples turning to Assisted Reproductive Technology. Thus, novel methods for improving sperm motility in vitro are required.

SUMMARY OF THE INVENTION

It has been surprisingly found that amorphous calcium carbonate (ACC) can positively enhance regeneration, development, maturation and differentiation of cells. In part this invention is based on the unexpected findings that ACC accelerates nerve fiber regeneration, promotes myotube formation, ameliorates the quality of sperm, and enhances development of embryos, including but not limited to increasing the number of embryos reaching advanced stages of development.

In one aspect, the present invention provides a pharmaceutical composition comprising amorphous calcium carbonate (ACC) stabilized by at least one stabilizing agent, for use in treating a disease or a condition related to neuromuscular defects. According to particular embodiments, the disease or condition is selected from a muscular dystrophy and an axonal defect. According to some embodiments, the pharmaceutical composition is for use in treating an axonal defect, e.g. axonal damage. According to another embodiment, the pharmaceutical composition is for use in treating a muscular dystrophy such as Duchenne muscular dystrophy. According to a further aspect, the present invention provides a method for treating a disease or a condition selected from a muscular dystrophy and axonal defect and in a subject in need thereof, comprising administering to said subject a pharmaceutically acceptable composition comprising amorphous calcium carbonate (ACC) stabilized by at least one stabilizing agent.

According to another aspect, the present invention provides a method for in vitro fertilization, comprising (a) in vitro fertilizing a mammalian oocyte; and (b) in vitro culturing the embryo(s), wherein step (a), step (b) or both steps (a) and (b) are performed in a cell culture medium comprising ACC stabilized by at least one stabilizing agent. The method, in some embodiments, may further comprise a step of in vitro maturation of an oocyte in a cell culture medium comprising ACC stabilized by at least one stabilizing agent, prior to step (a). According to some embodiments, the mammal is selected from human and non-human mammal.

According to certain aspects, the present invention provides a method for improving or ameliorating the quality of sperm, comprising exposing sperm to amorphous calcium carbonate (ACC) stabilized by at least one stabilizing agent. According to some embodiments, the method comprises exposing or contacting the sperm with ACC stabilized with at least stabilizing agent. According to one embodiment, the sperm is human sperm. According to another embodiment, improving the quality of sperm comprises enhancing sperm motility, enhancing sperm progressive motility, increasing sperm count, therefore, the method of the present invention comprises enhancing sperm motility, enhancing sperm progressive motility, increasing sperm count.

According to another embodiment, the present invention provides a method from separating sperm cells bearing X- and Y-chromosomes, said method comprising: (a) contacting a sperm sample with ACC stabilized by at least one stabilizer, (b) performing a swim-up procedure, (c) obtaining the fraction comprising the motile sperm, and (d) separating the upper phase and the lower phases of the fraction obtained in step (c), wherein the upper phase is enriched with Y-chromosome bearing sperm, and the lower phase is enriched with X-chromosome bearing sperm.

According to yet another aspect, the present invention provides a pharmaceutical composition comprising amorphous calcium carbonate (ACC) stabilized by at least one stabilizer, for use in treating male infertility.

According to some aspects, the present invention provides a method for treating male infertility in a subject in need thereof, comprising administering to said subject a pharmaceutical composition comprising an effective amount of amorphous calcium carbonate (ACC) stabilized by at least one stabilizer to said subject According to any one of the above aspects the ACC is stabilized by at least one stabilizing agent. According to one embodiment, the stabilizing agent is selected from polyphosphate, phosphorylated amino acids, organic acids, phosphorylated, phosphonated, sulfated or sulfonated organic compounds, phosphoric or sulfuric esters of hydroxyl-carboxylic acids, bisphosphonate, saccharides and derivatives thereof, proteins, phosphorylated proteins, natural and synthetic biopolymers and derivatives thereof, and any combinations thereof.

BRIEF DESCRIPTION OF THE FIGURES

FIG. 12 shows the effect of stabilized ACC on mice embryos development in vitro in cleavage medium.

DETAILED DESCRIPTION OF THE INVENTION

Figure 1:
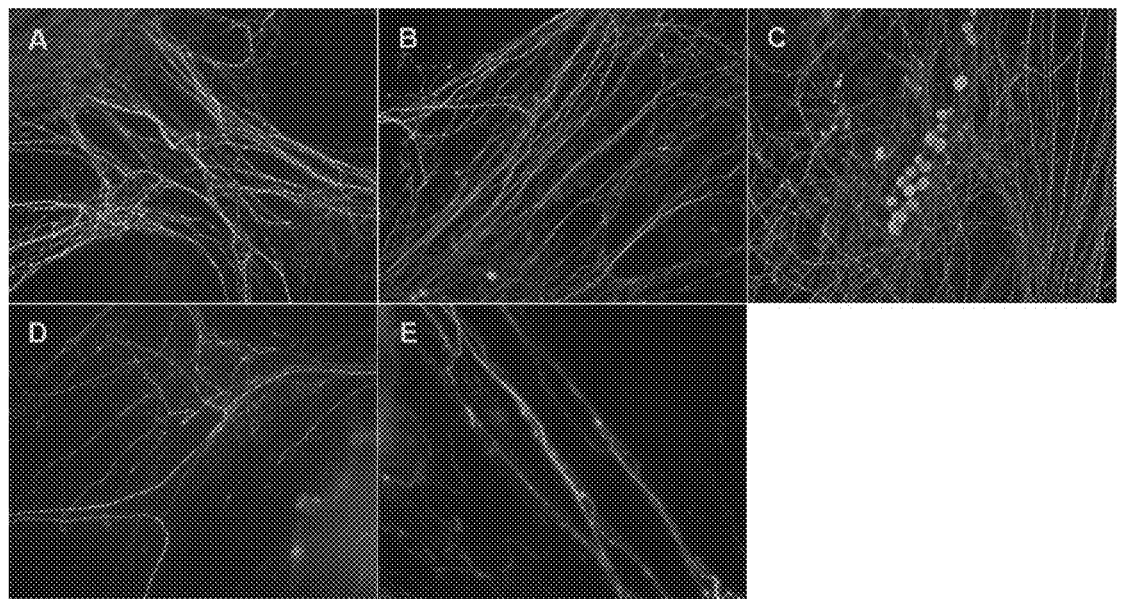
FIG. 1 shows the effect of different calcium sources on neuronal sprouting from cultured spinal cord-dorsal root ganglia (SC-DRG) slices. Immunofluorescent staining (anti neurofilament antibody) of nerve fibers grown from SC-DRG slices exposed to the following calcium compounds [$Ca^{2+}$ concentration of 2 mM]: (A) ACC-Etidronic Acid; (B) ACC-phosphoserine; (C) gastrolith; (D) crystalline calcium carbonate (CCC); and (E) $CaCl_2$ solution (control). Original magnification ×100.

The present invention discloses the unexpected advantages of ACC on cell growth and maturation. These attributes were observed in various systems of cell growth as are exemplified hereinbelow.

According to some particular aspects the present invention provides a pharmaceutical composition comprising amorphous calcium carbonate (ACC) stabilized by at least one stabilizing agent, for use in treating a disease or a condition selected from a neuromuscular disease or condition. In particular embodiments, the disease may be selected from muscular dystrophy and an axonal defect. According to some other particular aspects of the present invention, ACC stabilized by at least one stabilizing agent may be used in assisted reproductive technology (ART). According to one embodiment, the ART is in vitro fertilization. According to another embodiment, the ART comprises improving sperm quality.

For each aspect of the present invention individually and collectively the following terminology is used and the specific parameters are as defined hereinbelow:

The term "pharmaceutical composition" and "pharmaceutically acceptable composition" are used herein interchangeably and refer to a composition comprising ACC stabilized by at least one stabilizer, as disclosed herein below, formulated together with one or more pharmaceutically acceptable carriers.

The terms "pharmaceutically acceptable carrier" or "pharmaceutically acceptable excipient" as used herein refer to any and all solvents, dispersion media, preservatives, antioxidants, coatings, isotonic and absorption delaying agents, surfactants, buffer and the like, that are compatible with pharmaceutical administration. The use of such media and agents for pharmaceutically active substances is well known in the art. The compositions may contain other active agents providing supplemental, additional, or enhanced therapeutic functions.

According to some embodiments, the disease or a condition is an axonal defect, thus the present invention provides a pharmaceutical composition comprising ACC stabilized by at least one stabilizing agent, for use in treating an axonal defect.

The term "treating" as used herein refers to taking steps to obtain beneficial or desired results, including clinical results. Beneficial or desired clinical results include, but are not limited to, alleviation or amelioration of one or more symptoms associated with a condition.

Stabilized ACC:

According to any one of the above embodiments, the ACC is stabilized by at least one stabilizing agent. The term "amorphous calcium carbonate" and "ACC" are used herein interchangeably and refer to non-crystalline amorphous form of calcium carbonate stabilized by at least one stabilizing agent. The terms "stabilizing agent" and "stabilizer" are used herein interchangeably and refer to any substance that contributes to preserving calcium carbonate in the amorphous state during ACC production, formulating storage and/or use. In certain embodiments, the stabilizing agent is a single agent. In other embodiments, use of several stabilizing agents is encompassed. The terms "stabilized ACC" and "ACC stabilized by at least one stabilizer" may be used in some embodiments, interchangeably.

ACC may be obtained from a natural source or chemically synthesized. The terms also include naturally stabilized ACC such as ACC obtained from gastrolith.

The term "natural ACC" as used herein refers to any ACC isolated or derived from a natural source. Non-limiting examples of natural sources of ACC include gastroliths of freshwater crustaceans.

The term "synthetic ACC" as used herein refers to any ACC produced and/or derived by man ex-vivo.

The stabilizer may comprise a molecule having one or more functional groups selected from, but not limited to, hydroxyl, carboxyl, ester, amine, phosphino, phosphono, phosphate, sulfonyl, sulfate, or sulfino groups. The hydroxy bearing compounds, combined with the hydroxide, optionally also bear other functions like carboxyl, etc. but with the hydroxyl not being esterified.

According to some embodiments, the stabilizer has low toxicity or no toxicity to mammalian cells or organism, and in particular to a human being. According to other embodiments, the stabilizer is of food, nutraceutical or pharmaceutical grade.

In certain embodiments, the ACC stabilizing agent is independently at each occurrence, an organic acid; phosphorylated, phosphonated, sulfated or sulfonated organic compound; phosphoric or sulfuric ester of a hydroxyl carboxylic acid; an organoamine compound; an organic compound comprising a hydroxyl; an organophosphorous compound or a salt thereof; phosphorylated amino acids and derivatives thereof, a bisphosphonate; an organophosphate compound; an organophosphonate compound; organic polyphosphate, an inorganic polyphosphate, an inorganic phosphorous acid, an organic compound having multiple functional groups as defined above; an inorganic phosphate and polyphosphate compound; an organic compound having a polyphosphate chain; an organic surfactant; a bio-essential inorganic ion; saccharides and derivatives thereof, proteins, phosphorylated proteins, natural and synthetic biopolymers and derivatives thereof or any combination thereof. According to some embodiments, the stabilizer may have also a pharmaceutical activity, e.g. bisphosphonate, or ATP.

Thus in one embodiment, the stabilizing agent is selected from the group consisting of polyphosphate such as inorganic polyphosphate, organic acids, phosphorylated, phosphonated, sulfated or sulfonated organic compounds, phosphoric or sulfuric esters of hydroxy carboxylic acids, phosphorylated amino acids, bisphosphonate, organic polyphosphate, saccharides and derivatives thereof, proteins, peptides, phosphorylated proteins, phosphorylated peptides, and any combinations thereof. According to another embodiment, the stabilizing agent is selected from the group consisting of phosphoserine, adenosine triphosphate, adenosine diphosphate, phytic acid, citric acid, etidronic acid, pyrophosphate, polyphosphate, triphosphate, ethanol, hexamethaphosphate, chitin, and any combination thereof.

According to some embodiments, the stabilizer is an organic acid. According to certain embodiments, the organic acid is selected from ascorbic, citric, lactic or acetic acid, oxalic acid, malonic acid, glutaconic acid, succinic acid, maleic acid, lactic acid, glutamic acid, aconitic acid, and optionally include compounds having at least two carboxylic groups optionally having molecular weight not larger than 250 g/mol, such as citric acid, tartaric acid, malic acid, etc. According to one particular embodiment, the stabilizer is citric acid In another embodiment, the stabilizer is a phosphoric ester of hydroxyl carboxylic acids such as phosphoenolpyruvate. In another embodiment, the phosphoric or sulfuric esters of hydroxyl carboxylic acids comprise amino acids. Examples of such esters are phosphoserine, phosphothreonine, sulfoserine, sulfothreonine and phosphocreatine.

In another embodiment, the stabilizer is a saccharide. According to one embodiment, the saccharides is selected from mono-, di- tri-, oligo-, and polysaccharides like sucrose, mannose, glucose, chitosan and chitin. Stabilizer may be in some embodiments, a polyol such as glycerol. According to another embodiment, the stabilizer is an amino acid such as serine or threonine. Each possibility represents a separate embodiment, of the present invention.

Non-limiting Example of natural and synthetic biopolymers and derivatives are polynucleotides and glycoproteins.

Some specific unlimited examples for such ACC stabilizers that were approved for food consumption, found in natural food or in human beings include phytic acid, citric acid, sodium pyrophosphate dibasic, adenosine 5'-monophosphate (AMP) sodium salt, adenosine 5'-diphosphate (ADP) sodium salt and adenosine 5'-triphosphate (ATP) disodium salt hydrate, phosphoserine, phosphorylated amino acids, food grade surfactants, sodium stearoyl lactylate, and combinations thereof.

According to some embodiments, the stabilizer comprises at least one component selected from phosphoric or sulfuric esters of hydroxyl carboxylic acids, such as phosphoenolpyruvate, phosphoserine, phosphothreonine, sulfoserine or sulfothreonine and saccharides, selected from mono-, di-, tri-, oligo- and poly-saccharides, for example, sucrose, mannose, glucose. The hydroxyl bearing compound may further comprise at least one alkali hydroxide, such as sodium hydroxide, potassium hydroxide and the like. The phosphorylated acids may be present in oligopeptides and polypeptides. In other embodiments, of the invention, the stabilizer is an organic acid selected from monocarboxylic acid or multiple carboxylic acid, e.g. dicarboxylic acid or tricarboxylic acid. Each possibility represents a separate embodiment, of the invention. The organic acid may be as defined above.

In some embodiments, of the invention, the ACC stabilizer is selected from phosphorylated amino acids, polyols and combinations thereof. In some embodiments, the stable ACC comprises a phosphorylated compound as a stabilizer wherein the phosphorylation is performed on the hydroxyl group of an organic compound. In some embodiments, the stable ACC comprises a stabilizer selected from the group consisting of citric acid, phosphoserine, phosphothreonine and combinations thereof. The non-limiting examples of stabilizers containing phosphate, phosphite, phosphonate groups and salts or esters thereof include phytic acid, dimethyl phosphate, trimethyl phosphate, sodium pyrophosphate, tetraethyl pyrophosphate, ribulose bisphosphate, etidronic acid and other medical bisphosphonates, 3-phosphoglyceric acid salt, glyceraldehyde 3-phosphate, 1-deoxy-D-xylulose-5-phosphate sodium salt, diethylene triamine pentakis(methylphosphonic acid), nitrilotri(methylphosphonic acid), 5-phospho-D-ribose 1-diphosphate pentasodium salt, adenosine 5'-diphosphate sodium salt, adenosine 5'-triphosphate disodium salt hydrate, α-D-galactosamine 1-phosphate, 2-phospho-L-ascorbic acid trisodium salt, α-D-galactose 1-phosphate dipotassium salt pentahydrate, α-D-galactosamine 1-phosphate, 0-phosphorylethanolamine, disodium salt hydrate, 2,3-diphospho-D-glyceric acid pentasodium salt, phospho(enol)pyruvic acid monosodium salt hydrate, D-glyceraldehyde 3-phosphate, sn-glycerol 3-phosphate lithium salt, D-(-)-3-phosphoglyceric acid disodium salt, D-glucose 6-phosphate sodium salt, phosphatidic acid, ibandronate sodium salt, phosphonoacetic acid, DL-2-amino-3-phosphonopropionic acid or combinations thereof. The bio-essential inorganic ions may include, inter alia, Na, K, Mg, Zn, Fe, P, S, N; P or S in the phase of oxides; or N as ammonia or nitro groups.

The stabilizer may further include phosphonate compounds such as, but not limited to bisphosphonates, polyphosphates, such as, but not limited to pyrophosphate or polyphosphonates or organo polyphosphates, such as, but not limited to, adenosine diphosphate (ADP) or adenosine triphosphate (ATP).

Optionally ACC is stabilized by a combination of phosphoserine and citric acid. In another embodiment, the ACC is stabilized by triphosphate and citric acid.

The ACC may be stabilized by more than one stabilizers, e.g. two stabilizers. In some embodiments, the first stabilizer and the second stabilizer are similar. In other embodiments, the first stabilizer and the second stabilizer comprise different stabilizers. The first and the second stabilizers may be each independently as defined hereinabove. The stable ACC can comprise more than two stabilizers, wherein the stabilizers may be same or different. The stable ACC can comprise more than two stabilizers, wherein one or more stabilizers are added to the ACC during the formation and precipitation of the ACC; hence constituting "internal" stabilizers, and another one or more stabilizers are added at the ACC particle surfaces after their formation; hence, constituting "external" stabilizers. Further examples for stable ACC and the preparation thereof may be found in International Patent Applications Nos. WO 2009/053967, WO 2014/024191 and WO 2016/193982.

In some embodiments, the stabilizing agent is a protein or a peptide. In one embodiment, the protein or peptide is a naturally produced and purified protein or peptide. In another embodiment, the protein is synthetically produced protein. In some embodiments, the protein is selected from GAP65, GAP22, GAP21 and GAP12 proteins. In another embodiment, the proteins are selected from CqCDA1, chotinase 2, beta-N-acetylglucosaminidase, GAMP-like, chitinbinding protein, CqCBP, CAP10, GAP 18.2, GAP 02526, CqHc1, CqHc2, CqHc3, CqHc4, CqHc5, CqHc6, CqHc7, cryptocyanin1, cyclophilin, cystatin 1, cycstatin 2, LPS-BP, LEA protein and crystacyanin, optionally said proteins are originated from C. quadricarinatus. According to certain embodiments, the proteins are phosphorylated proteins In some embodiments, the stabilizing agent is selected from polyphosphate, phosphorylated amino acids, organic acids, phosphorylated, phosphonated, sulfated or sulfonated organic compounds, phosphoric or sulfuric esters of hydroxy carboxylic acids, bisphosphonate, saccharides, derivatives thereof, proteins, phosphorylated proteins, natural and synthetic biopolymers and derivatives thereof and any combinations thereof. In other embodiments, the stabilizing agent is selected from phosphoserine, triphosphate, adenosine triphosphate, adenosine diphosphate, phytic acid, citric acid, etidronic acid, pyrophosphate, ethanol, hexamethaphosphate, chitin, and any combination thereof.

In some embodiments, the stabilizing agent is selected from organic acids, phosphorylated organic acids, phosphoric or sulfuric esters of hydroxy carboxylic acids, phosphorylated amino acids, bisphosphonate, organic polyphosphate, saccharides, derivatives thereof, proteins and any combinations thereof.

According to some embodiments, the at least one stabilizer is selected from the group consisting of a polyphosphate, bisphosphonate, phosphorylated amino acid, citric acid, and any combination thereof. In some embodiments, more than one stabilizers, e.g. 2, 3 or 4 stabilizers are added.

According to some embodiments, the stabilizer is a polyphosphate or pharmaceutically acceptable salts thereof. According to some embodiments, the polyphosphate is physiologically compatible, water soluble polyphosphate salt selected from the group consisting of sodium, potassium and any other essential cation of polyphosphate. In one embodiment, the polyphosphate is organic or inorganic polyphosphate. The term "polyphosphate" as used herein refers to polymeric esters of $PO_4$. According to some embodiments, the polyphosphate is physiologically compatible water soluble polyphosphate salt selected from the group consisting of sodium and potassium polyphosphate. In some embodiments, the polyphosphate is an inorganic polyphosphate or pharmaceutically acceptable salts thereof. Not-limiting examples of such salt are Na, K, Mg, Mn and Zn. According to some embodiments, the inorganic phosphate comprise 2 to 10 phosphate groups, e.g. 2, 3, 4, 5, 6, 7, 8, 9, or 10 phosphate group. According to some embodiments, the polyphosphate is selected from pyrophosphate, triphosphate, and hexametaphosphate. According to one embodiment, the stabilizer is pyrophosphate or pharmaceutically acceptable salts thereof such as sodium pyrophosphate. According to another embodiment, the stabilizer is triphosphate or pharmaceutically acceptable salts thereof such as sodium triphosphate. The term "triphosphate" and "tripolyphosphate" are used herein interchangeably. According to a further embodiment, the stabilizer is hexametaphosphate or a pharmaceutically acceptable salt thereof such sodium hexametaphosphate.

According to some embodiments, the stabilizer is a bisphosphonate or pharmaceutically acceptable salts thereof. The not-limiting examples of salt are Na, K, Mg, Mn and Zn.

The term "bisphosphonate" as used herein refers to organic compounds having two phosphonate ($PO(OH)_2$) groups. The term further relates to compounds having a backbone of PO3-organic-PO3. Most typical is a series of bisphosphonates that are used as pharmaceuticals for treating osteoporosis. According to some embodiments, the bisphosphonate is selected from the group consisting of etidronic acid, zoledronic acid, medronic acid, alendronic acid and a pharmaceutically acceptable salt thereof. According to some embodiments, the stabilizer is an etidronic acid or a pharmaceutically acceptable salt thereof. According to another embodiment, the stabilizer is a zoledronic acid or a pharmaceutically acceptable salt thereof. According to a further embodiment, the stabilizer is a medronic acid or a pharmaceutically acceptable salt thereof. According to certain embodiments, the stabilizer is alendronic acid or a pharmaceutically acceptable salt thereof.

According to certain embodiments, the stabilizer is a phosphorylated amino acid. According to one embodiment, the phosphorylated amino acid is phosphoserine. According to another embodiment, the phosphorylated amino acid is phosphothreonine.

According to some embodiments, the ACC composition comprises a combination of the stabilizers disclosed above.

According to some embodiments, the stabilizer is polyphosphate or a bisphosphonate as defined hereinabove, and the molar ratio between P atoms of the stabilizer and Ca atoms of the ACC (P:Ca molar ratio) is about 1:90 to 1:1. In one embodiment, the P:Ca molar ratio is about 1:40 to about 1:1. In a further embodiment, the P:Ca molar ratio is about 1:35 to about 1:2. In certain embodiments, the P:Ca molar ratio is about 1:30 to about 1:3. In certain embodiments, the P:Ca molar ratio is about 1:28 to about 1:3. In other embodiments, the P:Ca molar ratio is about 1:25 to about 1:4. In further embodiment, the P:Ca molar ratio is about 1:20 to about 1:5. In another embodiment, the P:Ca molar ratio is about 1:20 to about 1:6. In a particular embodiment, the P:Ca molar ratio is about 1:15 to about 1:5. In another particular embodiment, the P:Ca molar ratio is about 1:25 to about 1:5. According to some embodiments, such polyphosphate is pyrophosphate, triphosphate, hexametaphosphate or a pharmaceutically acceptable salt thereof. According to another embodiments, the bisphosphonate is alendronic acid, etidronic acid, zoledronic acid or medronic acid and the P:Ca molar ratio is as defined hereinabove.

According to some embodiments, the calcium content (Ca content) stabilized ACC comprising polyphosphate or bisphosphonate is about 1 wt % to about 39 wt %, about 5 wt % to about 39 wt %, about 10% to about 39 wt %, about 15% to about 39 wt %, about 20 wt % to about 38 wt %, about 25 wt % to about 38 wt %, or about 30 to about 38. The terms "Ca content" and "calcium content" is used herein interchangeably and refer to the content of calcium of the ACC in the final composition.

In certain embodiments, the P:Ca molar ratio is about 1:40 to about 1:1, and the Ca content is about 20 wt % to about 39 wt %. In some embodiments, the molar ratio is 1:28 to about 1:3, and the Ca content is about 30 wt % to about 38 wt %. In another embodiment, the molar ratio is 1:25 to about 1:5, and the Ca content is about 30 wt % to about 36 wt %.

According to some embodiments, the stabilizer is selected from the group consisting of a polyphosphate, phosphorylated amino acid, bisphosphonate, citric acid, tartaric acid and any combination thereof. According to one embodiment, the polyphosphate is selected from the group consisting of triphosphate, pyrophosphate, and hexametaphosphate, the phosphorylated amino acid is phosphoserine or phosphothreonine, and the bisphosphonate is selected from the group consisting of alendronate, etidronic acid, zoledronic acid and medronic acid.

According to some embodiments, the stabilized ACC comprises less than 20 wt %, less than 15 wt %, less than 10 wt %, or less than 5 wt % of the stabilizing agent. In some embodiments, the stabilized ACC comprises up to 5 wt % of the stabilizing agent.

According to one embodiment, the average diameter of the stabilized ACC primary particles is about 10 nm to about 5 μm. According to another embodiment, the average diameter of the ACC primary particles is about 30 nm to about 400 nm. According to yet another embodiment, the average diameter average diameter of the ACC primary particles is about 30 nm to 350 nm. According to certain embodiments, the average diameter of the ACC primary particles is about 35 nm to 300 nm, 40 nm to about 250 nm, about 45 nm to about 200 nm, about 50 nm to about 150 nm or about 60 nm to about 100 nm. According to yet another embodiment, the average diameter of the ACC primary particles is about 30 nm to 00 nm. According to still another embodiment, the primary particles of ACC are aggregated and an average diameter of the aggregates is between 0.5 μm and 300 μm. According to one further embodiment, the diameter of aggregates of the ACC primary particle is about 1 to about 100 μm, about 10 to about 50 μm or about 20 to about 40 μm. According to another embodiment, the average diameter of the aggregates of the ACC primary particle is between 1 μm and 10 μm.

Pharmaceutical Compositions and Routes of Administration:

According to any one of the above embodiments, the pharmaceutical composition of the present invention may be administered by any known route of administration. The term "administering" or "administration of" a substance, a compound, an agent or a pharmaceutical composition to a subject can be carried out using one of a variety of methods known to those skilled in the art. For example, a compound, an agent or a composition can be administered enterally or parenterally. Enterally refers to administration via the gastrointestinal tract including per os, sublingually or rectally. Parenteral administration includes administration intravenously, intradermally, intramuscularly, intraperitoneally, subcutaneously, ocularly, sublingually, intranasally, by inhalation, intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some embodiments, the administration includes both direct administration, including self-administration, and indirect administration, including the act of prescribing a drug or a medical food. For example, as used herein, a physician who instructs a patient to self-administer a drug or a medical food, or to have the drug or the medical food administered by another and/or who provides a patient with a prescription for a drug or a medical food is administering the drug or a medical food to the patient. According to some embodiments, pharmaceutical composition is pharmaceutical food or food supplement.

In one embodiment, the pharmaceutical composition comprising stabilized ACC is administered via a systemic administration. For example stabilized ACC may be administered orally, sublingually or rectally. Alternatively the stabilized ACC may be administered intravenously, intradermally, intramuscularly, intraperitoneally, subcutaneously, ocularly, sublingually, intranasally, by inhalation, intraspinally, intracerebrally, and transdermally. In one specific embodiment, the stabilized ACC is administered orally.

The pharmaceutical composition according the present invention may be prepared in any known method. In particular, the pharmaceutical composition may be formulated using a method known in the art so as to provide rapid, continuous or delayed release of the active ingredient after administration. In one particular embodiment, the pharmaceutical composition is formulated as a solid dosage form selected from tablets, capsules, powder or granules. In another embodiment, the pharmaceutical composition is formulated as a liquid or semi-liquid dosage form selected from an elixir, tincture, suspension, syrup, emulsion or gel. The pharmaceutical composition may be formulated as semi-solid formulations such as gum.

Pharmaceutical compositions intended for oral use may be prepared according to any method known to the art for the manufacture of pharmaceutical compositions and may further comprise one or more agents selected from sweetening agents, flavoring agents, coloring agents and preserving agents in order to provide pharmaceutically elegant and palatable preparations. Tablets contain the active agent in admixture with non-toxic pharmaceutically acceptable excipients, which are suitable for the manufacture of tablets. These excipients may be, e.g., inert diluents such as calcium carbonate, sodium carbonate, lactose, calcium phosphate, or sodium phosphate; granulating and disintegrating agents, e.g., corn starch or alginic acid; binders; and lubricating agents. The tablets are optionally coated utilizing known techniques to delay disintegration and absorption in the gastrointestinal tract and thereby provide an extended release of the drug over a longer period.

Neuromuscular Diseases or Conditions:

According to one embodiment, the present invention provides a pharmaceutical composition comprising amorphous calcium carbonate (ACC) stabilized by at least one stabilizing agent, for use in treating an axonal defect.

The term "axonal defect" refers to any defect, damage or injury to the axonal part of a nerve cell of the peripheral or central nervous system. Nerves can be damaged either through trauma or disease. Traumatic nerve injury, such as carpal tunnel syndrome, is caused by the compression of nerves. Other trauma, such as falls and motor vehicle accidents, may lead to the severance of nerves. Diseases that harm nerves include multiple sclerosis, diabetes, spina bifida, and polio. Multiple sclerosis, for example, causes the breakdown of the insulating myelin surrounding axons. According to some embodiments, of the invention the defect or damage may occur to the brain, spinal cord, afferent and the efferent nerves emerging from the spinal cord and to peripheral nerves.

According to some embodiments, treating axonal defects comprises treating axonal damage such as injury. According to some further embodiments, treating axonal damage comprises enhancing regeneration and/or recovery of a damaged nerve. According to another embodiment, treating axonal damage comprises enhancing nerve regeneration. According to some embodiments, treating axonal defect comprises treating a defect resulted from a disease such as multiple sclerosis.

According to some embodiments, the axonal defect is an axonal damage, thus the pharmaceutical composition of the present invention is for use in treating an axonal damage, e.g. an axonal injury.

In one embodiment, treating of axonal damage comprises enhancing regeneration and/or recovery of a damaged nerve.

The terms "neuronal regeneration" and "nerve regeneration" as used herein may be used interchangeably and refer to recovery of functions of a damaged nerve. Specifically, it includes recovery of signaling via the nerve by repairing a damaged site, regrowth of axonal and dendritic neuronal fibers of the peripheral or the central nervous system. In some embodiments, nerve regeneration refers to sprouting from damaged neuronal fibers.

According to some embodiments, the locally administered pharmaceutical composition is formulated in a liquid or semi-liquid formulation as defined hereinabove. In one embodiment, the liquid or semi-liquid formulation is selected from a suspension, emulsion, colloid or gel. In one particular embodiment, the stabilized ACC is administered as a suspension.

The defected of damaged nerve may be a nerve of the peripheral nerve system (PNS) or of the central nerve system (CNS). Thus in one embodiment, the pharmaceutical composition of the present invention is for treating a damage to the nerves of the central nervous system. According to another embodiment, the pharmaceutical composition of the present invention is for treating a damage to the peripheral nervous system. According to some embodiments, of the invention, the pharmaceutical composition of the present invention is for treating a damage occurred to the brain, spinal cord, afferent and the efferent nerve emerging from the spinal cord, or to peripheral nerves.

According to one embodiment, the pharmaceutical composition is administered locally. In one more specific embodiment, the pharmaceutical composition is administered in proximity to the damaged nerve. According to some embodiments, the pharmaceutical composition is administered by injection, infusion or via a pump.

According to one embodiment, the pharmaceutical composition comprising ACC stabilized by least one stabilizing agent is selected from phosphoserine, triphosphate, adenosine triphosphate, adenosine diphosphate, phytic acid, citric acid, etidronic acid, pyrophosphate, ethanol, hexamethaphosphate, chitin, and any combination thereof, for use in treating an axonal defect such as axonal damage.

According to some embodiments, the disease or disorder is a muscular dystrophy. Thus in one embodiment, the present invention provides a pharmaceutically acceptable composition comprising stabilized ACC, for use in treating a muscular dystrophy.

The term "muscular dystrophy" as used herein refers to any one of several degenerative disorders, diseases or conditions characterized by progressive skeletal muscle weakness and fragility. Many of these diseases result from mutations in genes encoding proteins of the dystrophin-glycoprotein complex (DGC). In one embodiment, muscular dystrophy refers to a disease identified as Duchenne, Becker, limb-girdle, congenital, facioscapulohumeral, myotonic, oculopharyngeal, distal, or Emery-Dreifuss muscular dystrophy. In one particular embodiment, the muscular dystrophy is Duchenne muscular dystrophy (DMD). Thus in one embodiment, the pharmaceutically acceptable composition of the present invention is for use in treating DMD.

In one embodiment, the term treating refers to alleviation or amelioration of one or more symptoms associated with muscular dystrophy, delay or slowing of that impairment. According to some embodiments, treating muscular dystrophy comprises promoting myotube formation. The term "myotube formation" as used herein refers to a process in which myoblasts fuse into multi-nucleated fibers, myotube. According to some embodiments, the term treating muscular dystrophy further comprises also reducing the time to the onset of spontaneous contractile activity of said myotubes. The time to the onset of spontaneous contractile activity is defined as a time needed to myoblasts to fuse and start spontaneously contracting.

According to the teachings of the present invention, ACC is stabilized by at least one stabilizing agent as described herein above. According to one embodiment, the stabilized ACC is natural ACC obtained from a natural source, e.g. from gastrolith, or chemically synthesized.

According to one embodiment, the present invention provides a pharmaceutical composition comprising ACC stabilized by at least one stabilizing agent for use in treating DMD, wherein the stabilizing agent is selected from phosphoserine, triphosphate, adenosine triphosphate, adenosine diphosphate, phytic acid, citric acid, etidronic acid, pyrophosphate, ethanol, hexamethaphosphate, chitin, and any combination thereof. According to some embodiments, the stabilizing agent is selected from phosphoserine, triphosphate, bisphosphonate and combination thereof with citric acid. According to one embodiment, the pharmaceutical composition is administered systemically, e.g. orally.

According to another aspect, the present invention provides use of ACC stabilized by at least one stabilizing agent, for the preparation of a medicament for treatment of a disease or a condition selected from an axonal defect and muscular dystrophy.

Assisted Reproductive Technology:

According to some aspects the present invention, ACC stabilized by at least one stabilizing agent may be used in assisted reproductive technology (ART).

According to another aspect, the present invention provides a method for in vitro fertilization, comprising (a) in vitro fertilizing a mammalian oocyte; and (b) in vitro culturing the embryo(s), wherein step (a), step (b) or both steps (a) and (b) are performed in a cell culture medium comprising ACC stabilized by at least one stabilizing agent. According to one embodiment, the present invention provides a method for in vitro fertilization, comprising (a) in vitro fertilizing a mammalian oocyte; and (b) in vitro culturing the embryo(s) in a cell culture medium comprising ACC stabilized by at least one stabilizing agent. In another embodiment, the present invention provides a method for in vitro fertilization, comprising (a) in vitro fertilizing a mammalian oocyte in a cell culture medium comprising ACC stabilized by at least one stabilizing agent; and (b) in vitro culturing the embryo(s). In other embodiments, both steps, i.e. (a) in vitro fertilizing a mammalian oocyte; and (b) in vitro culturing the embryo(s) are performed in a cell culture medium comprising ACC stabilized by at least one stabilizing agent.

According to some embodiments, the cell culture media of steps (a) and (b) may in one embodiment, be different media. In another embodiment, said media may be the same medium.

The term "embryo" as used herein refers to a fertilized mammalian oocyte, i.e. a zygote, and to a multicellular organism developing from said zygote at its earliest stages of the development.

According to the teaching of the present invention, culturing embryo in a cell culture medium comprising ACC enhances embryo development. The terms "embryogenesis" and "embryo development" are used herein interchangeably and refer to the process by which the embryo forms and develops from the stage of a zygote to become an embryo, as known in the art, and includes the stages of reaching the stage of cleavage, compaction, blastocyst formation or blastocyst hatching. The terms "cleavage", "compaction", blastocyst" and "hatching" as used herein refer to the terms routinely used in embryology. The term "cleavage" is the division of cells in the early embryo. Producing a cluster of cells the same size as the original zygote. The different cells derived from cleavage are called blastomeres. The term "compaction" as used herein refers to the stage in which the dividing cells originated from a zygote maximize their contact with each other by polarization and adhesion, forming a compact ball that is held together by tight junctions. The term "blastocyst" as used herein refers to a structure which is developed after the compaction stage and comprising an inner cell mass, which subsequently forms the embryo, and the outer layer of the blastocyst, which surrounds the inner cell mass and a fluid-filled cavity called blastocoel. The term "hatching" as used herein refers to a stage at which the embryo emerges through its outer shell (zona pellucida).

The term "enhancing embryo development" as used herein refers to promoting, enhancing or improving the rate and/or the efficacy the development process as well as to the proportion of the successfully grown and maturated embryos. The enhancement is measured relatively to a control sample undergoing the same procedure but without the ACC in the cell culture medium. Thus in one embodiment, the method comprises in vitro culturing the embryo(s) in a cell culture medium comprising ACC stabilized by at least one stabilizing agent thereby enhancing embryo development and/or improving the quality of embryos.

The term "quality of embryos" as used herein refers to assessment of embryo development by any known and acceptable method. The embryo grading may differ with regards to selection of embryo stage and criteria for assessment of embryo quality. There are several stages for the evaluation of preimplantation embryo's quality. Some of these methods are described in Nasiri and Eftekhari-Yazdi (*Cell Journal*, 2015, 16(4), 392-405). In one embodiment, improving the quality of embryos comprises increasing the proportion of embryos reaching the stage of compaction, blastocyst formation or zona hatching.

The term "cell culture medium", "growth medium" and "culture medium" are used herein interchangeably and refer to a cell culture medium used for or capable of supporting the growth of cells, tissue or organs. The cell culture medium may be liquid, solid or semi-solid. Different cell culture media may have different properties and comprises different salts and nutrients, however all media are isotonic media and have an osmotic pressure suitable for cell growth. Thus, the cell culture medium is an isotonic cell culture medium. In one particular embodiment, the "growth medium" is suitable for growth embryos. Embryo cell culture medium is well known in art, and its content may vary according to e.g. the stage of the embryo, and a person skilled in the art would know to adapt the cell culture medium according to his needs. According to any one of the above embodiment, the ACC stabilized by at least one stabilizer may be added to any known medium suitable for oocytes and/or embryos growth or development. Non-limiting examples are monoculture media such as SAGE 1-Step™ and/or sequential Media such as Quinns Advantage™ Sequential Media (ORIGIO).

According to some embodiments, the method comprises a step of in vitro maturation of an oocyte in a cell culture medium comprising ACC stabilized by at least one stabilizing agent prior to step (a). Thus in one embodiment, the present invention provides a method for in vitro fertilization, comprising (a) in vitro maturation of an oocyte; (b) in vitro fertilizing a mammalian oocyte; and (c) in vitro culturing the embryo(s), wherein steps (a) and (b), steps (a) and (c), or steps (a), (b) and (c) are performed in a cell culture medium comprising ACC stabilized by at least one stabilizing agent.

According to the teaching of the present invention, culturing the oocyte in a cell culture medium comprising ACC stabilized by at least one stabilizer to enhances the oocyte maturation, therefore the method comprising enhancing oocyte maturation. The term "oocyte maturation" refers to the process and to each one of its stages, whereby an oocyte progresses from an immature state, being incapable of being fertilized, to an oocyte that is meiotically mature, being fertilizable and capable of producing a viable embryo. Enhancing of oocyte maturation refers to expedition of the process as well as to increasing the probability of the oocyte to reach the mature stage. Therefore, in one embodiment, the method comprises enhancing oocyte maturation. In other embodiments, the method comprises maturation of the oocyte and the embryo in a cell culture medium comprising ACC stabilized by at least one stabilizer, therefore enhancing the oocyte maturation and the embryo development.

The term "enhancing" as used herein refers to promoting, improving, augmenting, typically increasing the growth parameters, and being measured relatively to a control sample grown on the same medium but without the ACC.

According to any one of the above embodiment, the final concentration of stabilized ACC in the cell culture medium is about 0.1 to about 20 mM, about 0.5 to about 15 mM, about 1 to about 10 mM, about 2 to about 8 mM, about 3 mM to about 6 mM or about 4 mM to about 5 mM. According to one embodiment, the ACC is added at the final concentration of about 0.8 mM to about 5 mM or about 1.3 mM to about 3.5 mM, or at final concentration of about 1.7 mM to about 2.6 mM. In more particular embodiment, the stabilized ACC is present in a concentration of 0.5 to about 4 mM, about 1 to about 3 mM, about 1.5 to about 2.5, or about 1, 1.5, 2 or 2.5 mM. According to some embodiments, the concentration of stabilized ACC in the cell culture medium is about 0.0001% w/v to about 1% w/v about 0.0005% w/v to about 0.5% w/v, about 0.001% w/v to about 0.1% w/v, about 0.005% w/v to about 0.05% w/v, about 0.01% w/v to about 0.03% w/v.

According to one embodiment, contacting stabilized ACC with oocyte and/or embryo enhances embryo development and/or oocyte maturation by about 10% to about 300%, about 20% to about 250%, about 30% to about 200%, about 40% to about 150%, about 60% to about 100% or about 70% to about 90%. Enhancement by 100% meaning that the parameter, e.g. proliferation in increased 2 times; enhancement by 200% means that the parameter, e.g. embryo development, in increased 3 times, and so on. According to some embodiments, contacting stabilized ACC with oocyte and/or embryo enhances embryo development and/or oocyte maturation by 50% to about 300%, about 100% to about 250%, about 150% to about 250%.

According to some embodiments, enhancement of oocyte maturation and/or enhancement of embryo development enhances the outcome of the IVF. Therefore according to one embodiment, the present invention provides a method form enhancing IVF procedure, said method comprising exposing oocyte, exposing embryo(s) or exposing both oocyte and embryo to stabilized ACC.

According to another embodiment, the method further comprises retrieving at least one oocyte from a mammalian female and/or implanting the embryo(s) to the mammalian female.

In any one of the abovementioned embodiments, the embryo and/or oocyte is a human or non-human mammalian embryo and/or oocyte. In one particular embodiment, the embryo and/or oocyte is a human embryo and/or oocyte. In other embodiments, the embryo and/or oocyte is a non-human mammalian embryo and/or oocyte. Non-limiting examples of non-human mammalian embryo and/or oocyte are livestock animals, domestic pets, rodents, lagomorpha, buts and primate embryo and/or oocyte. In one embodiment, the non-human embryo is an embryo of livestock animals such as cattle, pigs, sheep, goats, horses, mules, donkeys, buffalo, or camels. In one particular embodiment, the embryo and/or oocyte is cattle embryo and/or oocyte. In some other embodiments, the domestic pet embryo and/or oocyte is a cat or dog embryo and/or oocyte; the rodent embryo and/or oocyte is an embryo and/or oocyte of a mouse, rat, guinea pig or hamster; the lagomorpha embryo and/or oocyte is a rabbit embryo and/or oocyte; and the primate embryo and/or oocyte is monkey such as macaques or ape such as chimpanzee.

According to any one of the above embodiment, ACC stabilized by at least one stabilizer may be added to any known medium suitable for oocytes and/or embryos development or maturation. Examples for such media are monoculture media such as SAGE 1-Step™ or sequential Media such as Quinns Advantage™ Sequential Media (ORIGIO).

According to one embodiment, the present invention provides a method for in vitro fertilization, comprising (a) in vitro fertilizing a mammalian oocyte; and (b) in vitro culturing the embryo(s), wherein step (a), step (b) or both steps (a) and (b) are performed in a cell culture medium supplemented with ACC stabilized by at least one stabilizing agent selected from phosphoserine, triphosphate, etidronic acid, pyrophosphate, ethanol, chitin hexametaphosphate, citric acid, and combination of phosphoserine, triphosphate, etidronic or hexametaphosphate with citric acid. According to another embodiment, the method comprises a step of in vitro maturation of an oocyte in a cell culture medium comprising ACC stabilized by at least one stabilizing agent, prior to step (a). Thus in one embodiment, the present invention provides a method for enhancing in vitro fertilization, comprising (a) in vitro maturation of an oocyte (b) in vitro fertilizing a mammalian oocyte; and (c) in vitro culturing the embryo(s), wherein steps (a) and (b), steps (a) and (c), or step (a), (b) and (c) are performed in a cell culture medium comprising ACC stabilized by at least one stabilizing agent. According to one embodiment, the media suitable for embryos growth are monoculture media such as SAGE 1-Step™ or sequential Media such as Quinns Advantage™ Sequential Media (ORIGIO). According to one embodiment, the ACC is added at the final concentration of about 0.8 mM to about 5 mM or about 1.3 mM to about 3.5 mM, or at the final concentration of about 1.7 mM to about 2.6 mM. According to one embodiment, the method comprises enhancing oocyte maturation and/or enhancing embryos development. According to another embodiment, the method comprises improving the quality of embryos and therefore increasing the rates of IVF success.

According to some embodiments, the present invention provides a method for in vitro embryo production comprising (a) fertilizing the oocyte(s) in vitro; and (b) growing the embryo(s) in vitro in an embryo culture medium comprising ACC stabilized by at least one stabilizing agent. According to some embodiments, the method comprises retrieving at least one oocyte from a mammalian female before step (a).

According to one aspect, the present invention provides a method for improving the quality of sperm, said method comprising exposing sperm to an effective amount of amorphous calcium carbonate (ACC) stabilized by at least one stabilizing agent.

The terms "sperm" and "spermatozoa" as used herein interchangeably refers to male reproductive cells. The term "sperm sample" refers to one or more samples comprising sperm. The sperm sample may be semen obtained from a subject or processed semen, liquefied semen, sedimented and optionally resuspended sperm, etc.

According to one embodiments, improving the quality of sperm is selected from the group consisting of enhancing sperm motility, enhancing sperm progressive motility, increasing sperm count, and any combination thereof.

The term "sperm motility" as used herein refers to the fraction of sperm moving among all the sperm cells in a given specimen sample. The term "progressive motility" as used herein refers to the fraction of sperm moving in an approximately constant direction. The terms "enhancing sperm motility" and "enhancing sperm progressive motility" as used herein, refer to increasing the fraction of motile sperm and of sperm having progressive motility, respectively. Therefore, in one embodiment, the present invention provides a method for enhancing sperm motility. According to another embodiment, the present invention provides a method for enhancing sperm progressive motility. The sperm motility, progressive motility and sperm maturation stage may be assessed by any known method in the art. For example the motility may be assessed by computer-assisted sperm analysis (CASA) method (Amann & Waberski, 2014, Theriogenology, 81: 5-17).

According to some embodiments, increasing sperm count comprises increasing the sperm count in motility or progressive motility procedure. According to one embodiments, the motility or progressive motility procedure is a swim up procedure.

The term "enhancing" is used as defined herein. According to some embodiments, enhancing sperm motility, enhancing sperm progressive motility, increasing sperm count comprises enhancing sperm motility, enhancing sperm progressive motility, increasing sperm count by about 10% to about 600%, about 20% to about 500%, about 30% to about 400%, about 40% to about 300%, about 50% to about 200, about 60% to about 150% or about 70% to about 100%. Enhancement by 100% meaning that the parameter, e.g. motility in increased 2 times. According to some embodiments, the motility or the sperm count are enhanced by about 100% to about 500%, about 120% to about 400%, about 150% to about 300%.

According to any one of the above embodiments, the sperm is a sperm of a human or non-human mammal. According to some embodiments, the non-human mammal is selected from the group consisting of livestock animals, domestic pets, rodents, wild animals and primate.

In one embodiment, the livestock animals is selected from cattle, pigs, sheep, goats, horses, mules, asses, buffalo, and camels. In some other embodiments, the domestic pet is a cat or dog, the rodent is rat, mice guinea pig or hamster, the lagomorpha is a rabbit, and the primate is monkey such as macaques or ape such as chimpanzee.

According to another embodiment, the sperm is a sperm of a non-mammal animal. According some embodiments, the non-mammal animal is selected from the group consisting fish, insects and birds.

According to one embodiment, the sperm is human sperm.

According to any one of the above embodiments, exposing cells to ACC stabilized by at least one stabilizing agent comprises adding said ACC to a cell culture medium. The term "exposing to" and "contacting with" are used herein interchangeably are refer to placing or transferring cells to in medium of an environment comprising the component such as stabilized ACC or adding the component, e.g. stabilized ACC to a medium in which the cells are grown or cultured, or adding stabilized ACC to the environment into which the sperm is placed. According to some embodiments, exposing to stabilized ACC comprises contacting cells with ACC within subject's body.

According to any one of the above embodiments, the ACC stabilized by at least one stabilizer may be added to any known medium suitable for sperm handling or maturation. According to some embodiments, the medium is selected from sperm separation medium such as ISolate®, PureCeption™, Multipurpose Handling Medium® (MHM®), medium for sperm wash such as Quinns™ Sperm Washing Medium, Multipurpose Handling Medium® (MHM®) and Modified HTF Medium with Gentamicin—HEPES, and medium for capacitation such as Biggers-Whitten-Whittingham (BWW) medium, Ham's-F10 and a modified Tyrode's medium (HSM).

According to any one of the above embodiment, the final concentration of stabilized ACC in the cell culture medium is about 0.1 to about 20 mM, about 0.5 to about 15 mM, about 1 to about 10 mM, about 2 to about 8 mM, about 3 mM to about 6 mM or about 4 mM to about 5 mM. According to one embodiment, the ACC is added at the final concentration of about 0.8 mM to about 5 mM or about 1.3 mM to about 3.5 mM, or at final concentration of about 1.7 mM to about 2.6 mM. In more particular embodiment, the stabilized ACC is present in a concentration of 0.5 to about 4 mM, about 1 to about 3 mM, about 1.5 to about 2.5, or about 1, 1.5, 2 or 2.5 mM. According to some embodiments, the concentration of stabilized ACC in the cell culture medium is about 0.0001% w/v to about 1% w/v about 0.0005% w/v to about 0.5% w/v, about 0.001% w/v to about 0.1% w/v, about 0.005% w/v to about 0.05% w/v, about 0.01% w/v to about 0.03% w/v.

According to any one of the above embodiment, the method further comprises use of the sperm in IVF or in intrauterine insemination.

According to a further aspect, the present invention provides a method for separating of X- and Y-chromosomes bearing sperm comprising: (a) contacting a sperm sample with ACC stabilized by at least stabilizer, (b) performing a progressive motility procedure, (c) obtaining the fraction comprising the motile sperm, and (d) separating the upper phase and the lower phases of the fraction obtained in step (c), wherein the upper phase is enriched with Y-chromosome bearing sperm, and the lower phase is enriched with X-chromosome bearing sperm. The method encompasses separation between sperm cells having X-chromosome and sperm cells having Y-chromosome.

According to one embodiment, the progressive motility procedure is a swim-up procedure. The swim-up procedure is well known in art. In general, a sperm sample is placed at the bottom of a tube and overlaid with sperm medium layer, the tube is incubated to about 1 hour at 37° C. allowing the motile sperm to move out the sample into sperm medium. The sperm medium is then collected and separated to the upper phase, enriched with Y-chromosome bearing sperm, and lower phase, enriched with X-chromosome bearing sperm. According to some embodiments, short incubation times, e.g. 10 to 30 min, can be used.

According to some embodiments, the method further comprises use of the upper phase and/or of the lower phase in IVF of in intrauterine insemination.

According to some aspects the present invention provides use of ACC stabilized by at least one stabilizing agent in assisted reproductive technology (ART). According to some embodiments, the ART is selected from in-vitro fertilization (IVF), sex selection, and sperm amelioration.

According to one embodiment, the present invention provides use of ACC stabilized by at least one stabilizing agent in IVF. According to one embodiment, the stabilized ACC is added to a cell culture at the stage selected from in vitro oocyte maturation, in vitro fertilizing a mammalian oocyte, in vitro culturing the embryo(s) or any combination thereof. Thus in one embodiment, the stabilized ACC is added to the cell culture medium at the stage of in vitro culturing the embryo(s). In another embodiment, the stabilized ACC is added to the cell culture medium at the stage of oocyte maturation. According to a further embodiment, the stabilized ACC is added during maturation of oocytes and during in vitro culturing the embryo(s). According to one embodiment, stabilized ACC enhances maturating of oocytes and/or embryo development.

According to another embodiment, the present invention provides use of ACC stabilized by at least one stabilizing agent in improving sperm quality. According to some embodiments, improving the quality of sperm is selected from the group consisting of enhancing sperm motility, enhancing sperm progressive motility, increasing sperm count, and any combination thereof. According to some embodiments, the sperm obtained by this method may be used in intrauterine inseminations or in IVF.

According to another embodiment, the present invention provides use of ACC stabilized by at least one stabilizing agent in sex selection technique. According to one embodiment, the sex selection technique comprises a step or enriching the sperm sample with sperm bearing one type of sex chromosome. This step comprising (a) contacting a sperm sample with ACC stabilized by at least one stabilizer, (b) performing a swim-up procedure, (c) obtaining the fraction comprising the motile sperm, and (d) separating the upper phase and the lower phases of the fraction obtained in step (c), wherein the upper phase is enriched with Y-chromosome bearing sperm, and the lower phase is enriched with X-chromosome bearing sperm.

According to another embodiment, the present invention provides ACC stabilized by at least one stabilizing agent for use in assisted reproductive technology (ART). According to some embodiments, the ART is selected from in-vitro fertilization (IVF), sex selection, sperm amelioration.

According to one embodiment, the stabilized ACC is for use in IVF. According to one embodiment, the stabilized ACC is for use in the stage selected from vitro oocyte maturation, in vitro fertilizing a mammalian oocyte, in vitro culturing the embryo(s), and any combination thereof. According to some embodiments, the stabilized ACC is added to the medium selected from a medium for in vitro oocyte maturation, a medium for in vitro fertilizing a mammalian oocyte, and a medium for in vitro culturing the embryo(s), as defined hereinabove.

According to another embodiment, the stabilized ACC is for use in improving sperm quality. According to some embodiments, the method comprises exposing sperm to stabilized ACC. According to some embodiments, improving the quality of sperm is selected from the group consisting of enhancing sperm motility, enhancing sperm progressive motility, increasing sperm count, and any combination thereof. According to some embodiments, the sperm obtained by this method may be used in intrauterine inseminations or in IVF.

According to a further embodiment, the stabilized ACC is for use in sex selection technique. According to one embodiment, the stabilize ACC is used for separating sperm bearing X- and Y-chromosomes by: (a) contacting a sperm sample with ACC stabilized by at least one stabilizer, (b) performing a swim-up procedure, (c) obtaining the fraction comprising the motile sperm, and (d) separating the upper phase and the lower phases of the fraction obtained in step (c), wherein the upper phase is enriched with Y-chromosome bearing sperm, and the lower phase is enriched with X-chromosome bearing sperm.

According to any one of the above embodiments, contacting the oocytes or sperm with stabilized ACC comprises adding stabilized ACC to a cell culture medium, as defined hereinabove.

According to any one of the above embodiment, the final concentration of stabilized ACC in the cell culture medium is about 0.1 to about 20 mM, about 0.5 to about 15 mM, about 1 to about 10 mM, about 2 to about 8 mM, about 3 mM to about 6 mM or about 4 mM to about 5 mM. According to one embodiment, the ACC is added at the final concentration of about 0.8 mM to about 5 mM or about 1.3 mM to about 3.5 mM, or at final concentration of about 1.7 mM to about 2.6 mM. In more particular embodiment, the stabilized ACC is present in a concentration of 0.5 to about 4 mM, about 1 to about 3 mM, about 1.5 to about 2.5, or about 1, 1.5, 2 or 2.5 mM. According to some embodiments, the concentration of stabilized ACC in the cell culture medium is about 0.0001% w/v to about 1% w/v about 0.0005% w/v to about 0.5% w/v, about 0.001% w/v to about 0.1% w/v, about 0.005% w/v to about 0.05% w/v, about 0.01% w/v to about 0.03% w/v.

According to another aspect, the present invention provides a pharmaceutical composition comprising amorphous calcium carbonate (ACC) stabilized by at least one stabilizer, for use in treating male infertility.

According to some embodiments, the male infertility is selected from male infertility caused by low sperm count and male infertility low sperm motility. The term "low sperm motility" refers to a condition in which the number of motile sperm for IUI is less than 5 million.

According to some embodiments, the pharmaceutical composition may be administered by any known method as described hereinabove. According to one embodiment, the pharmaceutical composition is administered orally.

According to one aspect, the present invention provides a method for treating male infertility in a subject in need thereof, comprising administering a pharmaceutical composition comprising amorphous calcium carbonate (ACC) stabilized by at least one stabilizer to said subject.

According to another aspect, the present invention provides a method for treating a disease or a condition selected from a muscular dystrophy and axonal defect in a subject in need thereof, comprising administering to said subject a pharmaceutically acceptable composition comprising amorphous calcium carbonate (ACC) stabilized by at least one stabilizing agent.

The terms "pharmaceutically acceptable composition", "ACC", "stabilizing agent", "axonal defect", and "muscular dystrophy" are as defined hereinabove.

According to one embodiment, the present invention provides a method for treating an axonal defect in a subject in need thereof, comprising administering to the subject a pharmaceutically acceptable composition comprising a therapeutically effective amount of ACC stabilized by at least one stabilizing agent. According to one embodiment, the axonal defect is axonal damage, e.g. axonal injury. According to certain embodiments, the axonal defect or damage is to nerves of the central nervous system or to nerves of the peripheral nervous system. According to some embodiments, treating axonal damage comprises enhancing recovery and/or regeneration of a damaged nerve.

According to some embodiments, administering comprises administering the pharmaceutically acceptable composition via systemic administration or local administration, as described above. According to some embodiments, systemic administration comprises enteral administration, i.e. via the gastrointestinal tract, e.g. per os, sublingually or rectally, and parenteral administration e.g. intravenously, intradermally, intramuscularly, intraperitoneally, subcutaneously, ocularly, sublingually, intranasally, by inhalation, intraspinally, intracerebrally, and transdermally. According to one embodiment, the pharmaceutical composition is orally administered. According to other embodiments, the administration is local administration, in particular in proximity to the defected, damaged or injured nerve. According to one embodiment, the pharmaceutically acceptable composition is locally administered by injection, infusion or via a pump.

According to another embodiment, the present invention provides a method for treating an muscular dystrophy in a subject in need thereof, comprising administering the subject a pharmaceutically acceptable composition comprising a therapeutically effective amount of ACC stabilized by at least one stabilizing agent. According to some embodiments, the muscular dystrophy is selected from the group consisting of Duchenne, Becker, limb-girdle, congenital, facioscapulohumeral, myotonic, oculopharyngeal, distal, and Emery-Dreifuss muscular dystrophy. In one particular embodiment, the muscular dystrophy is Duchenne muscular dystrophy (DMD).

Methods for Enhancing Cell Growth:

According to some aspects, the present invention provides a method for enhancing cell growth, comprising exposing cells to ACC stabilized by at least one stabilizer.

The term "growth" as used herein encompasses any of the following: proliferation, maturation, propagation, regeneration, differentiation, development and any combination thereof and may be used differently in accordance to the type of cells.

As defined hereinabove, the term "enhancing" refers to promoting, improving, augmenting, typically increasing the growth parameters, and being measured relatively to a control sample grown on the same medium but without the ACC. Thus in one embodiment, the method comprises enhancing proliferation, enhancing maturation, enhancing propagation, enhancing regeneration, enhancing maturation, and/or enhancing differentiation of cells. In one embodiment, enhancing growth comprises improving quality of cells, e.g. improving the quality of embryos. According to another embodiment, enhancing growth comprises enhancing two or more of the above parameters, e.g. enhancing proliferation and differentiation.

According to any one of the above embodiments, the cells are eukaryotic cells. According to some embodiments, the eukaryote cells are selected from animal, plant and insect cells.

According to one embodiment, the cells are animal cells. According to some embodiments, the animal cells are the cells of human or non-human mammal. According to certain embodiments, the non-human mammal is selected from livestock animals such as cattle, pigs, sheep, goats, horses, mules, donkeys, buffalo, or camels; a domestic pet e.g. a cat or dog; a rodent such as a mouse, rat, guinea pig or hamster; a lagomorpha such as a rabbit; and primates such as a monkey (e.g. macaques) or an ape (e.g. chimpanzee).

According to further embodiments, the cells are selected from nerve, muscle, epithelial, bone, adipose, stem cells, gamete cells, blood cells and embryos.

According to one embodiment, the present invention provides a method for enhancing growth of muscle cells. According to another embodiments, enhancing growth of muscle cells comprises enhancing myotube formation.

The term "myotube formation" as used herein refers to a process in which myoblasts fuse into multi-nucleated fibers, myotube.

According to some embodiments, the method comprises also reducing the time to the onset of spontaneous contractile activity of said myotubes. The time to the onset of spontaneous contractile activity is defined as a time needed to myoblasts to fuse and start spontaneously contracting.

In one embodiment, the myocytes formed from said myoblasts are selected from skeletal myocytes or cardiac myocytes. In more particular embodiment, myocytes are skeletal myocytes.

According to some embodiments, the method comprises enhancing myotube formation and/or the onset of contractility in skeletal muscle cell e.g. in case of Duchenne muscular dystrophy.

According to other embodiments, the method comprises enhancing growth of nerve cells. In one embodiment, enhancing growth of nerve cells comprises enhancing and acceleration nerve cells regeneration. Thus in one embodiment, the method comprises enhancing regrowth of axonal and dendritic neuronal fibers, of the peripheral and the central nervous system, and/or sprouting from damaged neuronal fibers.

According to some embodiments, the method comprises enhancing the maturation of cell, e.g. enhancing in vitro maturation of an oocyte. According to some embodiments, the oocyte is selected from human oocyte and non-human mammalian oocyte. The non-human mammalian is selected from livestock animals such as cattle, pigs, sheep, goats, horses, mules, donkeys, buffalo, or camels; a domestic pet e.g. a cat or dog; a rodent such as a mouse, rat, guinea pig or hamster; a lagomorpha such as a rabbit; and primates such as a monkey (e.g. macaques) or an ape (e.g. chimpanzee).

According to other embodiments, the method comprises improving the quality of embryos cultured in vitro, or enhancing embryo development. The term "quality of embryos" is used hereinabove. In one embodiment, improving the quality of embryos comprises increasing the proportion of embryos reaching a stage selected from the group consisting of compaction, blastocyst formation and blastocyst hatching stages. In another embodiment, improving the quality of embryos comprises accelerating the normal embryogenesis as measured by the time to reach a stage selected from the group consisting of compaction, blastocyst formation and blastocyst hatching stage.

According to some embodiments, the embryo is selected from human embryo of non-human mammalian embryo. The non-human mammalian is selected from livestock animals such as cattle, pigs, sheep, goats, horses, mules, donkeys, buffalo, or camels; a domestic pet e.g. a cat or dog; a rodent such as a mouse, rat, guinea pig or hamster; a lagomorpha such as a rabbit; and primates such as a monkey (e.g. macaques) or an ape (e.g. chimpanzee).

The enhancement of proliferation, maturation, propagation, regeneration, development and/or differentiation of cells, tissues or organs may be measured as percent of enhancement in comparison to the control as defined hereinabove. Therefore, according to one embodiment, the cell culture medium supplemented with stabilized ACC is capable of enhancing the growth parameters by about 10% to about 600%, about 20% to about 500%, about 30% to about 400%, about 40% to about 300%, about 50% to about 200, about 60% to about 150% or about 70% to about 100%. Enhancement by 100% meaning that the parameter, e.g. proliferation in increased 2 times; enhancement by 200% means that the parameter, e.g. embryo development, in increased 3 times, and so on. According to some embodiments, the growth parameters are enhanced by about 100% to about 500%, about 120% to about 400%, about 150% to about 300%.

According to some embodiments, the method comprises enhancing stem cells differentiation. According to one embodiment, the method comprises enhancing stem cells proliferation. According to further embodiment, the method comprises enhancing stem cells differentiation and proliferation. The term "stem cells" refers to cells which have the capacity to proliferate and differentiate into different cell types. According to some embodiments, the stem cells are selected from embryonic, chorionic, amniotic, hematopoietic, mesenchymal, neural, glial, adult and induced pluripotent stem cells. According to one embodiment, the stem cells are embryonic stem cells. According to another embodiment, the stem cells are hematopoietic stem cells. According to a further embodiment, the stem cells are mesenchymal stem cells. According to yet another embodiment, the stem cells are pluripotent stem cells stem cells. According to some embodiments, the stem cells are human stem cells. According to another embodiment, the stem cells are non-human mammal stem cells. According to one embodiment, the method comprises enhancing differentiation of stem cells such as MBA13 to osteoblasts.

According to some embodiments, the cell culture medium is suitable for growth of animal, plant or insect cells. According to one embodiment, the cell culture medium may be a natural medium or an artificial medium. According to some embodiments, the natural medium comprises biological fluid selected from plasma, serum, lymph, human placental cord serum, and amniotic fluid. According to another embodiment, the natural medium comprises tissue extracts such as extract of liver, spleen, tumors, leucocytes and bone marrow, extract of bovine embryo and chick embryos. According to a further embodiment, the natural medium comprises coagulants or plasma clots. According to some embodiments, the medium is an artificial medium supplemented. According to one embodiment, the artificial medium is a balanced salt solution. Examples of balanced salt solution are PBS, DPBS, HBSS, EBSS Tyrode's T6, WM1, Pool's P1, Quinn's HTF, and Gardner's G1. According to another embodiment, the artificial medium is a basal medium. According to some embodiments, the medium may be further supplemented as well known in the art. According to one embodiment, the medium is supplemented with serum, e.g. fetal bovine serum. According to a further embodiment, the artificial medium is a complex medium.

The term "basal medium" as used herein refers to a nutrient mixture of inorganic salts, sugars, amino acids, optionally also containing vitamins, organic acids and/or buffers. Basal media together with supplements provide the nutrients necessary to support cell life, growth and reproduction. The choice of basal medium used should be appropriate for the culture.

According to one embodiment, the artificial medium is a serum free medium. According to a further embodiment, the artificial medium is a cell culture medium with reduced serum content. According to another embodiment, the artificial medium is a protein-free media Examples of the cell media to which the stabilized ACC may be added and used according to the present invention are Dulbecco's Modified Eagle's Medium (DMEM), Minimum Essential Medium (EMEM), RPMI 1640 medium (developed at Roswell Park Memorial Institute), and Basal Medium Eagle (BME). Further examples of media according to the present invention are Ham's Nutrient Mixtures such as Ham's F-10, Ham's F-12, DMEM/F-12 (DMEM and Ham's F-12). Other examples are Iscove's Modified Dulbecco's Medium (IMDM), opti-MEM and Glasgow's MEM (GMEM). Examples of media suitable for insect cells growth are IPL-41 Insect Medium, Schneider's *Drosophila* medium, Grace's Insect medium, Serum-free Insect Media, Sf-900, TC-10, Shields and Sang M3 Insect Medium, TC-100 Insect Medium, TNM-FH Insect Medium and IPL-10. Examples of media suitable for embryos growth are monoculture media such as SAGE 1-Step™ or sequential Media such as Quinns Advantage™ Sequential Media (ORIGIO). Examples of media suitable for plant cell growth are Murashige and Skoog (MS), B5, N6 and Nitsch's medium.

Other examples of media are Modified Medium, NCTC Medium, MegaCell Media, Claycomb, Click's Medium, L-15 Medium, Medium 199, MCDB Media, Ames' Media, BGJb Medium (Fitton-Jackson Modification), Click's Medium, CMRL-1066 Medium, McCoy's 5A Modified Medium, NCTC Medium, Swim's S-77 Medium, Waymouth Medium, William's Medium E and in vitro fertilization media such as Global®, GM501, SSM™, Cleavage K-SICM, Blastocyst K-SIBM, Quinns Advantage®Cleavage, Quinns Advantage®Blastocyst, FERTICULT™IVF Medium, FERTICULT™ G3 Medium, IVC-TWO™, IVC-THREE™, ECM®, MultiBlast®, EmbryoAssist™, BlastAssist™, ISM1, ISM2, G-1™PLUS, G-2™PLUS, IVF™, and CCM™. Further examples of media are media for sperm separation such as ISolate®, PureCeption™, Multipurpose Handling Medium® (MHM®), media for sperm wash such as Quinns™ Sperm Washing Medium, Multipurpose Handling Medium® (MHM®) or Modified HTF Medium with Gentamicin. and media for maturation which enables the culture of immature oocytes to fully developed embryos suitable for transfer.

Thus according to one embodiment, the cell culture medium is selected from DMEM, RPMI 1640, MEM, IMDM, L-15 Medium (Leibovitz), MCDB Medium, Medium 199, opti-MEM and DMEM/F-12, Schneider's *Drosophila* medium, Grace's Insect medium, IPL-41 Insect Medium Sf-900, Serum-free Insect Media, Shields and Sang M3 Insect Medium, TC-100 Insect Medium, TNM-FH Insect Medium, Ham's F-12, Ham's F-10, GMEM, Ames' Medium, Basal Medium Eagle (BME), Claycomb, Click's Medium, Glasgow Minimum Essential Medium (GMEM), MegaCell Media, McCoy's 5A Modified Medium, NCTC Medium, Williams' Medium E, Waymouth Medium, TC-10 and IPL-10 medium. According to another embodiment, the cell culture medium is selected from DMEM, RPMI 1640, MEM, IMDM, opti-MEM, GMEM, Ham's F-12 and DMEM/F-12, Schneider's *Drosophila* medium, Grace's Insect medium, Sf-900, TC-10, IPL-10 medium and Media for sperm separation, wash or maturation e.g. selected from ISolate®, PureCeption™, Multipurpose Handling Medium® (MHM®), Quinns™ Sperm Washing Medium, Multipurpose Handling Medium® (MHM®) and Modified HTF Medium with Gentamicin.

In any one of the above embodiments, the term "comprising" includes the meaning of "consisting" and may be substituted by it.

As used herein, the term "about", when referring to a measurable value such as an amount, a temporal duration, and the like, is meant to encompass variations of +/−10%, or +/−5%, +/−1%, or even +/−0.1% from the specified value.

Having now generally described the invention, the same will be more readily understood through reference to the following examples, which are provided by way of illustration and are not intended to be limiting of the present invention.

EXAMPLES

Example 1. Effects of ACC on SC-DRG Co-Cultures

Methods

Culture Medium

The culture medium was composed of: 90% Dulbecco's modified eagle medium-nutrient mixture F-12 (DMEM-F12) calcium depleted (medium without calcium ions, (special preparation), 10% heat-inactivated fetal bovine serum (FBS), 6 g/L D-glucose, 2 mM glutamine, 25 µg/mL gentamicin and 0.05 ng/mL insulin-like growth factor 1 (IGF-I) (all purchased from Biological-Industries, Israel).

NVR-Gel as a Substrate for Neuronal Cultivation

Neural and Vascular Reconstruction Gel (NVR-Gel, NVR Labs proprietary) is composed of two main components: high molecular hyaluronic acid (HA, $3\times10^6$ Da, BTG, Israel) and laminin (Sigma). For neuronal cell cultivation, NVR-Gel of 1% was diluted with culture medium to a final concentration of 0.3-0.5%. The gel has the texture of a viscous liquid, it adheres easily and successfully the embedded cells or explants to the plastic or glass substratum, and enabled nerve fiber outgrowth in a 3D pattern.

Preparation of Neuronal Tissue Cultures

All the experiments were carried out and authorized by the local ethics committee recognized by the Israeli authorities for animal experimentation. Stationary organotypic cultures of dorsal root ganglia (DRG) and spinal cord (SC) as well as cultures of dissociated brain cells were prepared from rat fetuses (15 days of gestation, Lewis inbred, Harlan, Israel). Immediately after dissection, the isolated tissues were cut with a Macwain tissue chopper into small slices (of 400 µm thickness). In these studies, two tissue culture strategies were used. In the first method, tissue slices were seeded directly in 12 well-culture plates containing 1 mL culture medium containing 0.3%-0.5% NVR-Gel. In the second method, the tissue slices were further dissociated with a trypsin-EDTA solution for 30 min, and washed with a culture medium. Subsequently, the dissociated cells were added to a suspension of chitosan powder or gastrolith powder (micro carriers, MCs) and incubated in suspension at 37° C. for 4 days. The formed floating cells/MCs aggregates were then collected and seeded in 12 well-culture plates containing 1 mL of culture medium containing 0.3%-0.5% NVR-gel.

$Ca^{2+}$ Supplement Source $Ca^{2+}$ source (listed below) at final concentration of 1 or 2 mM was added once to the gel at the seeding stage and then to the nutrient medium at each consecutive feeding. Calcium source were as following: ACC-Etidronic Acid (ACC-ET) (fresh suspension); ACC-Phosphoserine (ACC-PS) (fresh suspension); Gastrolith (dissolved with 0.1 M HCl and then neutralized with NaOH 1M); gastrolith powder; CCC—Aqueous suspension of crystalline calcium carbonate (commercial nanoparticles powder); and $CaCl_2$) solution—control.

The cultures were monitored by daily phase contrast microscopic observations starting from 24 hours after setting the cultures onward.

Suspensions of fresh ACC preparations consisted of particles forming a stable suspension. The gastrolith is a natural ACC isolated from crabs, and can be purchased only as a dry powder. In this form, its other characteristic components (such as calcium ions and proteins) are not available to the cells. In order to increase their bioavailability, the gastrolith powder was dissolved in 0.1 M HCl (which mimics the acidity which exists in the stomach) and then neutralized with 1M NaOH.

Immunofluorescent Staining of Neuronal Cultures

After removal of the culture medium, the dorsal root ganglia (DRG) cultures were washed with phosphate buffered salt solution (PBS) and fixed in 4% paraformaldehyde for 15 min, and then washed again with PBS. The fixed cells were permeabilized with 0.1% of Triton X-100 in PBS and then immuno-blocked (to avoid non-specific staining) with a 1% bovine serum albumin (BSA) in PBS for 1 h at room temperature. The specimens were then incubated with rabbit anti-neurofilament antibodies (NF, Novus Biologicals, 1:500) to visualize the neurite outgrowth. The primary antibodies were diluted in 0.1% BSA and 0.05% Tween-20 in PBS (diluents buffer) and incubated with the specimens overnight at 4° C. After rinsing with 0.05% Tween-20 in PBS (wash buffer), the DRG specimens were incubated for 1 h at room temperature with the secondary antibodies Alexa-Fluor-594-conjugated donkey anti-rabbit IgG (Jackson ImmunoResearch, USA, 1:800 in a diluent buffer). Finally, the samples were rinsed again with wash buffer, and mounted with mounting medium (Immco Diagnostic, USA). All of the images were observed with an Olympus IX70 microscope.

Results

The effect of various calcium preparations was examined in SC-DRG co-cultures. In general, the cultures contained 400 micron SC slices with attached or separated slices of DRG. It can be said that all of the examined ACC preparations (ACC-ET, ACC-PS, and gastrolith) enhanced significantly neuronal fiber regeneration in comparison to CCC and the $CaCl_2$). Table 1 shows the portion of explants (out of 6) which exhibited nerve fiber sprouting after 4 days of cultivation in the presence of the various calcium preparations ($Ca^{2+}$ concentration of 2 mM) or in the presence of stabilizers alone (the stabilizer was added at the concentration of 0.05% to each well (from a stock solution of 5%)). It can be seen that the most intensive sprouting was observed in cultures which were exposed to ACC-ET (100% of explants), followed by ACC-PS and Gastrolith (66.6% of explants). The CCC and $CaCl_2$) induced neuronal sprouting only from 50% of the explants, and the stabilizers alone even a lower percentage (0-33%) During the establishment of the cultures (after the first week of cultivation) the regenerated nerve fibers became longer, thicker and ramified, until the formation of neuronal networks, mainly in cultures exposed to the various ACC preparations (FIG. 1).

TABLE 1

The effect of ACC preparations on early nerve fiber sprouting from SC-DRG co-cultures.

| Type of calcium preparation | Cultures with axonal regeneration (%) |
|---|---|
| ACC-ET (fresh suspension) | 100 |
| ACC-PS (fresh suspension) | 66.6 |
| Gastrolith | 66.6 |
| CCC (crystalline calcium carbonate) | 50 |
| $CaCl_2$ aqueous solution (control) | 50 |
| ET | 33.3 |
| PS | 0 |

Example 2. Effects of ACC on Brain Cultures

Figure 2:
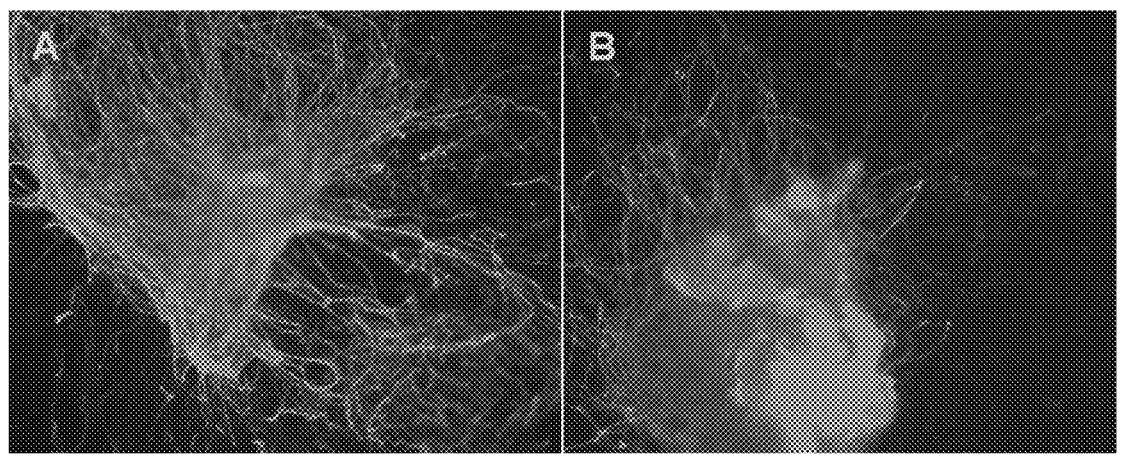
FIG. 2 shows the effect of (A) ACC-stabilized by Etidronic Acid and (B) $CaCl_2$ solution (control) on neuronal sprouting from brain cells cultured on chitosan microcarriers (MCs). Immunofluorescent staining of nerve fibers (anti neurofilament antibody) grown from brain cells-chitosan MCs aggregates, after 30 days in culture in the presence of 2 mM of either ACC-Etidronic Acid or $CaCl_2$ is presented.

The effect of ACC was studied on cultures of brain cells-MCs aggregates seeded in gel after 4 days in suspension (see methods part of Example 1). The results are presented in FIG. 2 and show that the ACC enhanced nerve fibers regeneration, significantly more than the calcium chloride. This is especially notable when comparing the number and the length of nerve fibers between the two treatments.

Example 3—Effects of ACC Preparations on Healthy Skeletal Muscle Cells

Methods

Preparation of Skeletal Muscle Cultures

Stationary skeletal muscle cultures were prepared from healthy 1 day new born rat (Sprague Dawley, Harlan, Israel). The muscle tissue was dissected from posterior legs and was thoroughly minced. Digestion was performed with Trypsin-EDTA while gentle trituration. After 30 min the supernatant, containing dissociated cells, was collected and a fresh Trypsin-EDTA was added. This procedure was repeated two more times. Then, all supernatants were pooled, centrifuged, and the cell pellet was re-suspended in Proliferation Medium. Cells were seeded in a Gelatin coated 12 wells culture plates, $1 \times 10^5$ cells/well containing 1 mL of Proliferation Medium. Two days later, the medium was changed to Fusion Medium, which was then changed twice a week. The cultures were monitored by daily phase contrast microscopic observations from 24 hours after setting the cultures and onward. At predetermined days, cultures were fixed in methanol for 20 minutes and then stained with Giemsa in order to evaluate the number of myotubes formed with time in cultures.

Culture Plates Coating with Gelatin

Stock solution of 1% porcine gelatin in water, was sterilized by autoclave. Once cooled, 500 µl of the solution were added to each well of the 12-wells culture plat. After incubation for 20 min at room temperature, the excess solution was removed, and the cells were seeded.

Proliferation Medium

For the proliferation stage, cells were cultured in: DMEM/F12 (containing 1 mM $Ca^{2+}$)+10% FBS, 25 µg/mL Gentamycin, and 2 mM L-Glutamine.

Fusion Medium

For the fusion stage the Proliferation Medium was changed with Fusion Medium, which was prepared as following: DMEM/F12 (containing 1 mM Ca2+), 2% horse serum (HS), 2 mM L-Glutamine, 25 µg/mL Gentamycin, and 4 units/100 mL Insulin (all purchased from Biological-Industries, Israel).

List of Tested Calcium Preparations

The fusion medium was enriched with the various calcium preparations listed in Table 2, at $Ca^{2+}$ concentration of 1 mM (since the medium already contained 1 mM of calcium ions, the final concentration of $Ca^{2+}$ was 2 mM). Control cultures were grown without further added calcium, or cultures enriched with free (soluble) stabilizer. The experiment was blinded by marking the various calcium preparations with arbitrary numerals only.

The components were added in one of the following ways: (i) aqueous suspensions of dry material; (ii) aqueous suspension of fresh material (before drying), or (iii) dissolved with HCl (to mimic the acidity which exists in the stomach. After dissolving was accomplished, the formed solutions were neutralized with 1M NaOH).

TABLE 2

| List of tested materials | |
|---|---|
| Added Substance | Total calcium concentration (mM) including 1 mM $Ca^{2+}$ ions of the medium |
| ACC-Etidronic Acid (ACC-ET) | 2 |
| ACC-Pyrophosphate (ACC-PyP) | 2 |
| ACC-Phospho serine (ACC-PS) | 2 |
| ACC-Adenosine triphosphate (ACC-ATP) | 2 |
| ACC-Adenosine diphosphate (ACC-ADP) | 2 |
| ACC-Phytic acid | 2 |
| ACC-Citric acid | 2 |
| Crystalline calcium carbonate (CCC) (commercial available powder) | 2 |
| $CaCl_2$ aqueous solution | 2 |
| ET | 1 |
| PyP | 1 |
| PS | 1 |
| ATP | 1 |
| ADP | 1 |
| Phytic acid | 1 |
| Citric acid | 1 |
| Control | 1 |

Results

Effect of Dry ACC on Healthy Skeletal Muscle

Figure 3:
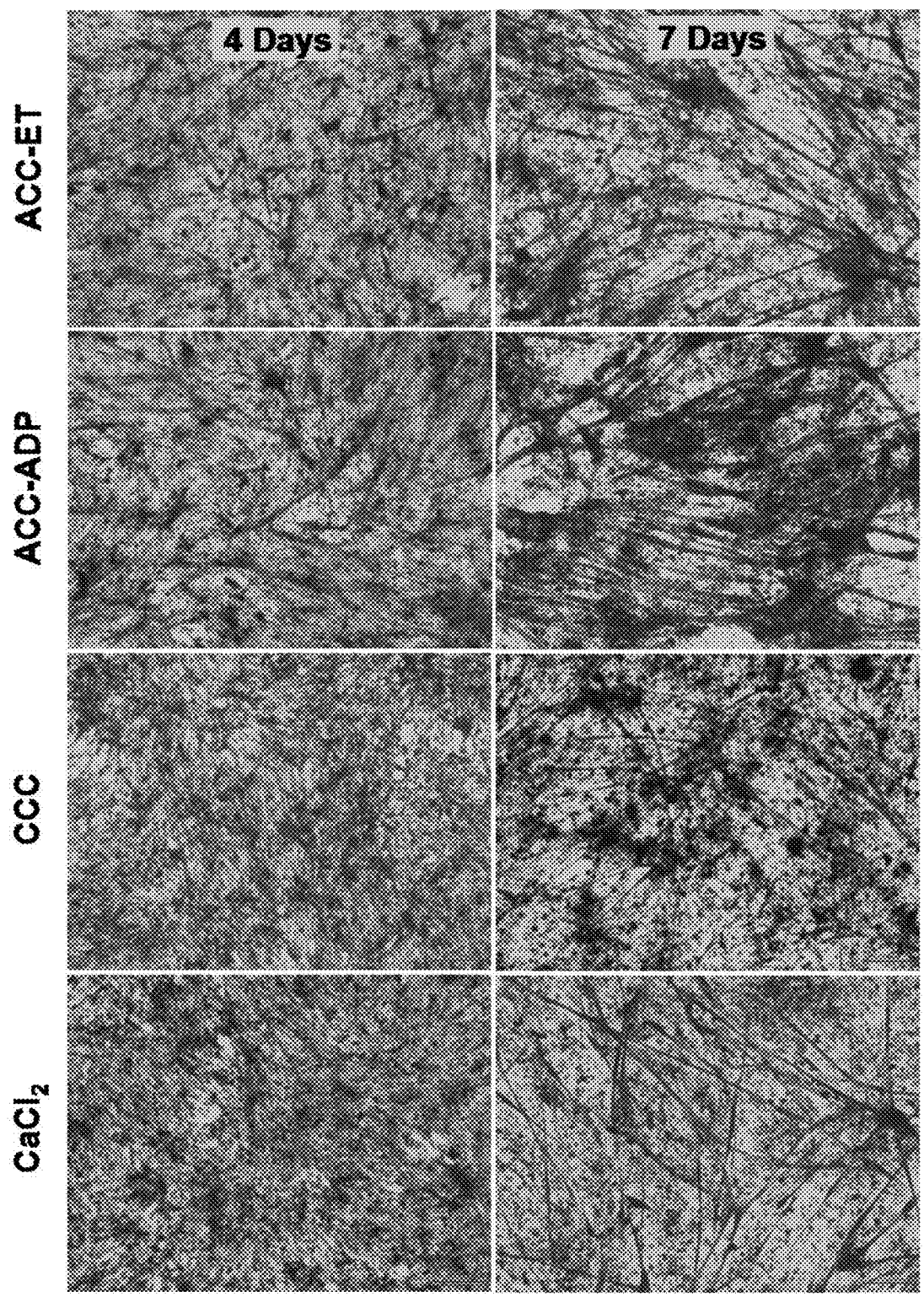
FIG. 3 shows the effect of ACC on formation of myotubes in healthy skeletal muscle cultures. Original magnification ×40. Skeletal muscle cultures were exposed to the following calcium compounds (final $Ca^{2+}$ concentration of 2 mM): ACC-Etidronic Acid; ACC-ADP; Gastrolith; crystalline calcium carbonate (CCC); and $CaCl_2$ solution (control). Cultures were fixed after 4 and 7 days and stained with Giemsa. Enhancement of myotubes formation by skeletal muscle cultures was observed in ACC treated cells.

In the first stage, dry ACC powder was used. The powder (listed in Table 2 according to the stabilizers used in their preparation) were suspended in water, and then added to the culture media in the concentration of 1 mM. Since the medium already contained 1 mM of calcium ions, then the final concentration of $Ca^{2+}$ was 2 mM. The results, some of which are shown in FIG. 3 (left hand side), revealed that cultures which were exposed to ACC exhibited early formation of many myotubes already within 4 days of cultivation, with no significant differences between the different ACC preparations. In control cultures, which were exposed to added CCC or $CaCl_2$, myotubes formation was observed later. After 7 days, the cultures that were treated with ACC exhibited numerous long and thick muscle fibers, while in cultures treated with CCC and $CaCl_2$, fewer, thinner and shorter muscle fibers were developed (FIG. 3; right hand side).

It is also noted, that in cultures exposed to ACC preparations, muscle contractions were observed already on day 7 after seeding, while in cultures exposed to added CCC or $CaCl_2$) muscle contractions appeared only after 10 days or more.

It was concluded from the above in vitro results that all ACC preparations enhance myotubes formation and early muscle contractility of the healthy striated muscle cultures.

Example 4—Evaluating the Effect of ACC on Duchenne Muscular Dystrophy Muscle Cell Line—In Vitro Studies Methods Mdx Cells Preparation The influence of the different calcium preparations was investigated on the mdx cell line (Duchenne muscular dystrophy model), which was kindly provided by Prof. (Emeritus) David Yaffe from the Weizmann Institute of Science, Israel.

Cells from the Mdx cell line were seeded in a Gelatin coated 12 wells culture plate, $3 \times 10^4$ cells/well containing 1 mL of Proliferation Medium. Two days later (~66% confluence), the medium was changed to Fusion Medium which was changed twice a week. The various calcium preparations were separately added to the Fusion Medium according to the treatment described in Table 3. Cultures were enriched with the various calcium preparations, at $Ca^{2+}$ concentration of 1 mM. Since the medium already contained 1 mM of calcium ions, then the final concentration of Ca2+ was of 2 mM.

TABLE 3

| Calcium sources | |
|---|---|
| Treatment | Calcium source (2 mM) |
| Control | $CaCl_2$ |
| ACC-ET | Amorphous Calcium Carbonate-Etidronic Acid |
| ACC-PS | Amorphous Calcium Carbonate-Phospho Serine |

The effects of the tested calcium preparations on cell proliferation, fusion to form myotubes and muscle contraction were monitored by daily phase contrast microscopic observation. At predetermined days, cultures were fixed in methanol for 20 minutes and then stained with Giemsa in order to evaluate the number of myotubes formed with time in cultures.

Creatine Kinase (CK) Analysis in Muscle Tissue Culture

In muscle cell cultures, CK is an indicator of myotubes formation and CK level increases (in tissue culture plates) in direct correlation with the progression of myotubes formation in muscle cultures. At predetermined days, cells were collected from culture wells (using a rubber policeman) and kept in 1 mL PBS (without $Ca^{2+}$) at −70° C. until analyzed. For CK measurement cell samples were thawed and physically lysed using a sonicator, to release the CK from muscle myotubes. CK concentration was determined using Creatine Kinase Activity Assay Kit (CK-NAC REAGENT SET, CURTISS, CHEM-INDEX INC, Hialeah, Fla., USA).

Results

Figure 4:
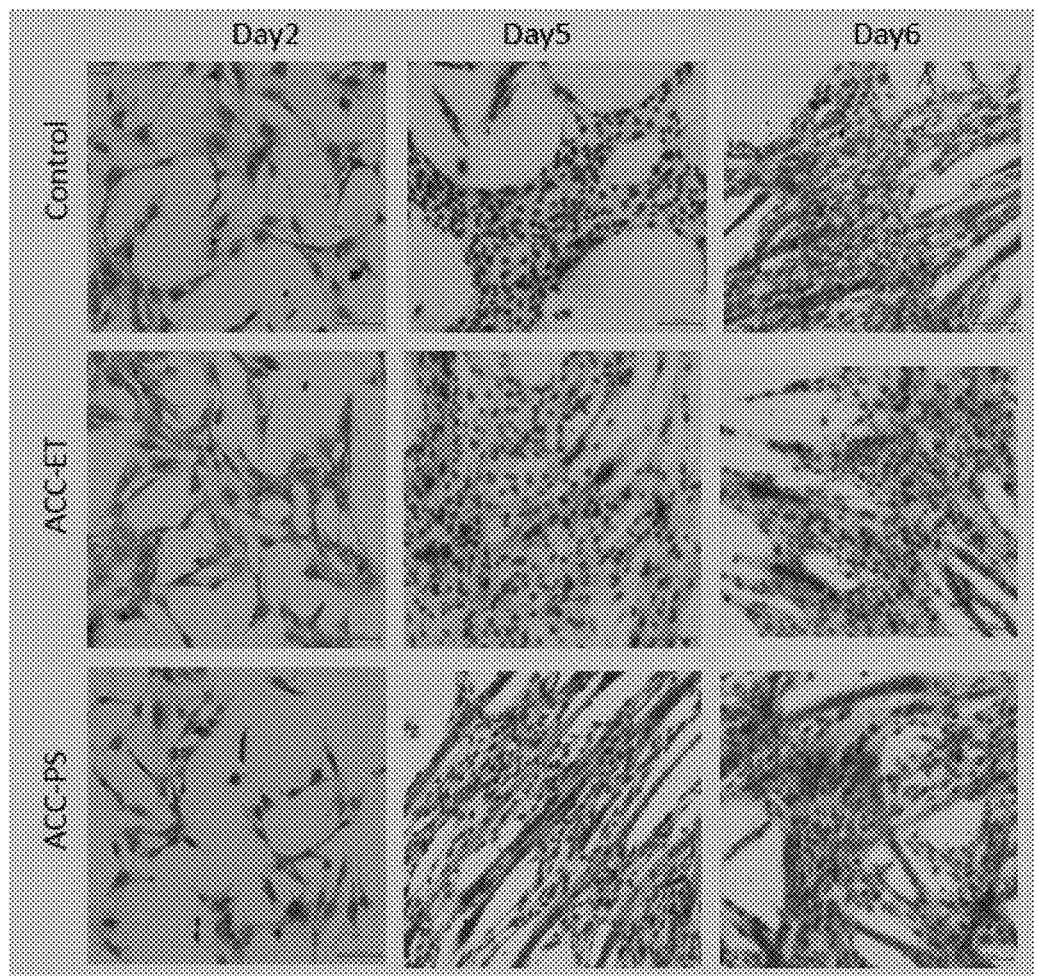
FIG. 4 shows the effect of ACC in the culture medium on early formation of myotubes in mdx cell line cultures. Giemsa staining of the cultures that were exposed to medium containing $CaCl_2$, ACC-ET and ACC-phosphoserine (ACC-PS) is shown. Original magnification ×100.
Figure 5:
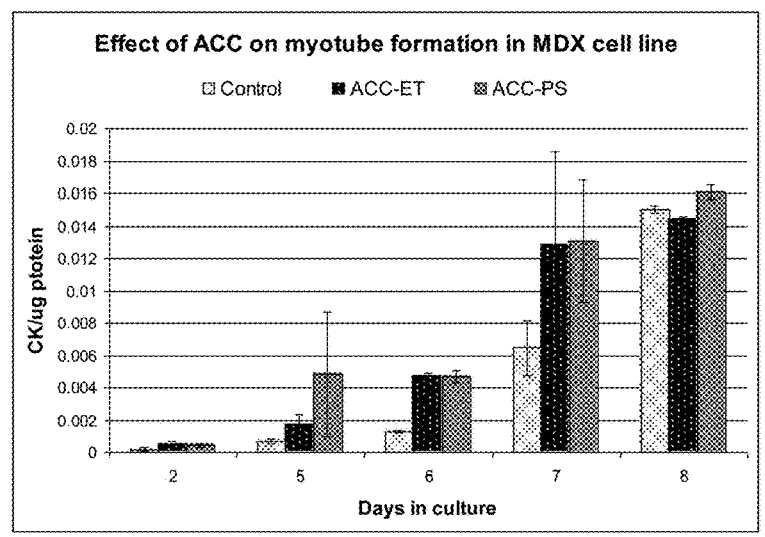
FIG. 5 shows the creatinine kinase (CK) levels as measured in mdx muscle cell line exposed to two ACC preparations (ACC-ET and ACC-PS) versus $CaCl_2$.

The results of the above experiments are presented in FIGS. 4 and 5. As it can be clearly seen, addition of ACC enhanced cell fusion and formation of myotubes better than the addition of a conventional calcium ion source ($CaCl_2$)).

This surprising result was demonstrated in both biochemical (CK activity) and morphological (microscopy) analysis (FIGS. 4 and 5). Moreover, the cultures exposed to ACC preparations, muscle contractions were observed already on day 7 after seeding, while in the controls it appeared only after 10 days or more. Therefore, it is concluded that ACC supplementation has a potential to treat DMD patients.

Example 5—the Effect of Calcium Sources on Primary Mdx Mouse Cells

Method
Extraction of Primary Cells

Thigh muscles were removed from the posterior legs of newborn (one day old) mdx mice under sterile conditions, and washed in PBS to remove excess of blood cells. The muscles were minced into small fragments. For enzymatic dissociation, the muscle fragments were placed in a bicker containing trypsin-EDTA solution (0.25 mM). To ensure cell separation, the mixture was placed on a stirrer, at room temperature, at gentle stirring for 20 min. The soup was collected and centrifuged at 300×g for 5 min. The pellet was re-suspended in DMEM containing FBS. The trypsinization steps were repeated for 3 more cycles. All supernatants were combined into one tube. Cell separation was determined visually (using phase contrast microscopy). Cells density was determined by using hemocytometer.

Cells were plated in a 12 wells plate in the concentration of $2 \times 10^5$ cells/well. The medium used was DMEM/F12 W/O $Ca^{2+}$ with the addition of 15% FBS and, 2 mM L-Glutamine Gentamicin (25 μg/ml). Calcium was separately added to the medium according to the treatment as describes in Table 4. At day 2 (~66% confluence) the medium was changed to fusion medium (DMEM/F12 without $Ca^{2+}$ with the addition of 10% HS, Insulin (4 units/100 ml) and Gentamicin (25 μg/ml)). Medium was changed every 3 days.

TABLE 4

Calcium sources used in primary cells study

| Treatment | Calcium source (2 mM) |
|---|---|
| Control | CaCl$_2$ |
| ACC-PP | Amorphous Calcium Carbonate stabilized by Polyphosphate |
| ACC-PS | Amorphous Calcium Carbonate stabilized by Phosphoserine |

Cell proliferation and fusion were qualitatively daily monitored. Cultures were fixed at days 2, 3, 4, 5 and 7 and stained with Giemsa, or using Myosin antibody.

Results

Figure 6:
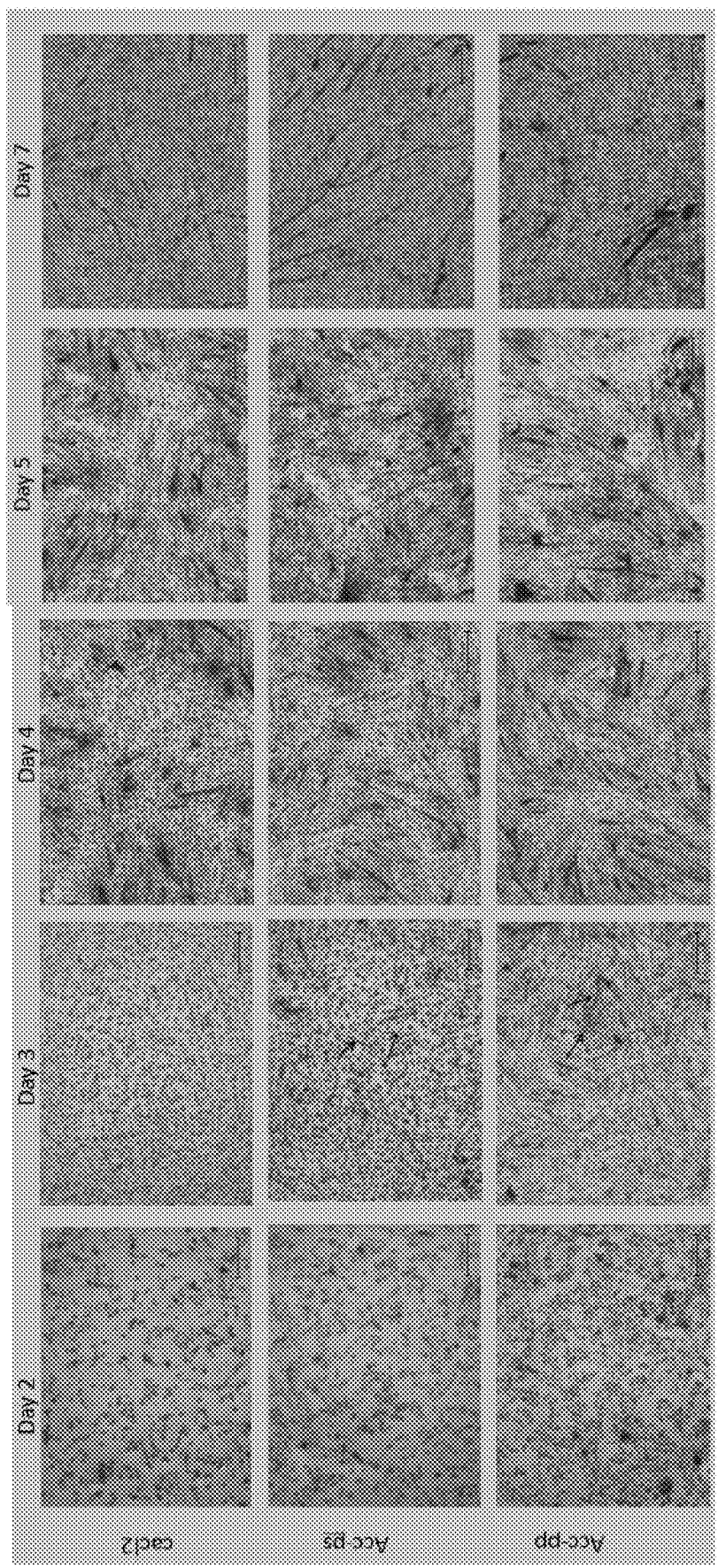
FIG. 6 shows the effect of ACC (ACC-PS, ACC-PP vs. control ($CaCl_2$)) on the formation of myotubes in mdx mice primary cultures (Giemsa staining; original magnification ×50).
Figure 7:
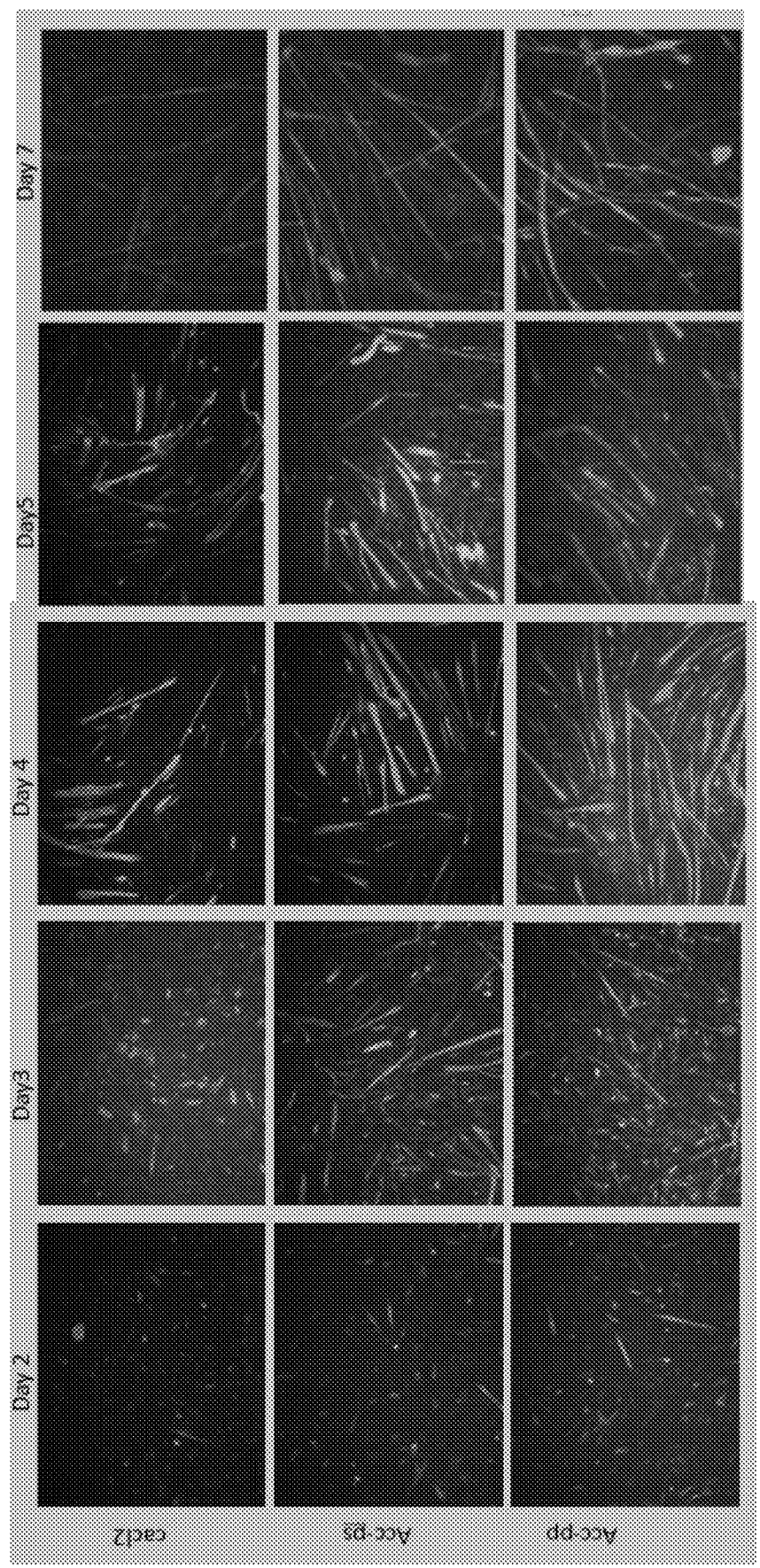
FIG. 7 shows the effect of ACC on formation of myotubes in mdx mice primary cultures demonstrated by myosin immunostaining; control ($CaCl_2$); ACC-PS, ACC-polyphosphate (ACC-PP). Original magnification ×100.

The results are presented on FIGS. 6 and 7. The beneficial effect of ACC formulations was demonstrated by myotubes formation, specifically at early time points, days 3 and 4 compared to control. Differences in the formed myotubes became indistinguishable at days 5 and 7. There was a high correlation between the Giemsa staining and the staining for myosin.

Example 6—Evaluating the Effect of ACC on Muscular Dystrophy in Mice—In Vivo Studies Experimental mice were administrated orally (by feeding or drinking) with control or test items. The control or test items were repeatedly administered daily until the study termination (after 12 weeks).

TABLE 5

Study Design

| Group No. | Strain | n= | Treatment Details |
|---|---|---|---|
| 1M | C57BL | n = 3 | Rodent commercial diet (Teklad) |
| 2M | mdx | n = 12 | Rodent commercial diet (Teklad) |
| 3M | | n = 12 | Low Calcium Diet (TDK95027, Harlan Inc) containing 1% elemental calcium from synthetic CCC ad libitum |
| 4M | | n = 12 | Low Calcium Diet (TDK95027, Harlan Inc) containing 1% elemental calcium from synthetic ACC (5% PS) ad libitum |
| 5M | | n = 12 | Water containing 0.06% elemental Calcium from synthetic ACC (10% PP) ad libitum |

PS—stabilized with phosphoserine
PP—stabilized with polyphosphate

Test System:
Species: Mice
Mdx Strain: C57/Bl 10 ScSn/DMD mdx/J
Wild type Strain: C57BL/6JOIaHsd.
Gender & Age: Males, 3 weeks of age at study initiation
Body Weight: Weight variation of animals at study initiation should not exceed ±5% of the mean weight of the gender.
Housing: Animals before study initiation were housed in polyethylene cages measuring 42.5×26.5×18.5 cm, with stainless steel top grill facilitating pelleted food and drinking water in plastic bottle and filled with wood shavings (Harlan Teklad Aspen/Sani-chips bedding) as bedding material. Bedding material were changed along with the cage at least once a week.
Identification: Ear tag and cage cards.
Termination: At the end of the study, animals were euthanized by $CO_2$ asphyxiation.
Justification: The MDX mice are a common animal model for evaluating the Duchenne Muscular Dystrophy (DMD).
Study Initiation Definition
The first control or test items administration were defined as "Day 1".
Study End Definition
The study was terminated 12 weeks from beginning.
Humanitarian Endpoint
Animals that were found in a moribund condition and animals showing severe pain or enduring signs of severe distress were humanely euthanized. Animals showing a decrease of body weight larger than 20% from the initial body weight were reported.
Test Items Administrations
Animals were administrated with ACC by food or by drinking. Animals were administrated with CCC by food. Control was administrated by feeding. The control or test items were repeatedly administered daily until study termination.
Tests and Evaluations
Morbidity and Mortality Observation
Observations for signs of morbidity and mortality were performed daily at study termination.
Body Weight Measurements
Body weight measurements were recorded once a week and at study termination, 12 weeks.
Blood Collection and Serum Preparation for Creatinine Kinase (CK) Levels:
At study termination blood sample was drawn from all animals under light anesthesia with Ketmaine/Xylazine, directly from the retro orbital sinus.

200 µl blood were collected into a yellow-cup tube with clotting activator gel. The tubes were kept at room temperature for at least 30 minutes for clotting and centrifuged at room temperature for 10 minutes at 4000 RPM. The serum samples are stored at 2-4° C. until delivered to CK analysis at A.M.L labs.

Creatinine Kinase—Results

Figure 8:
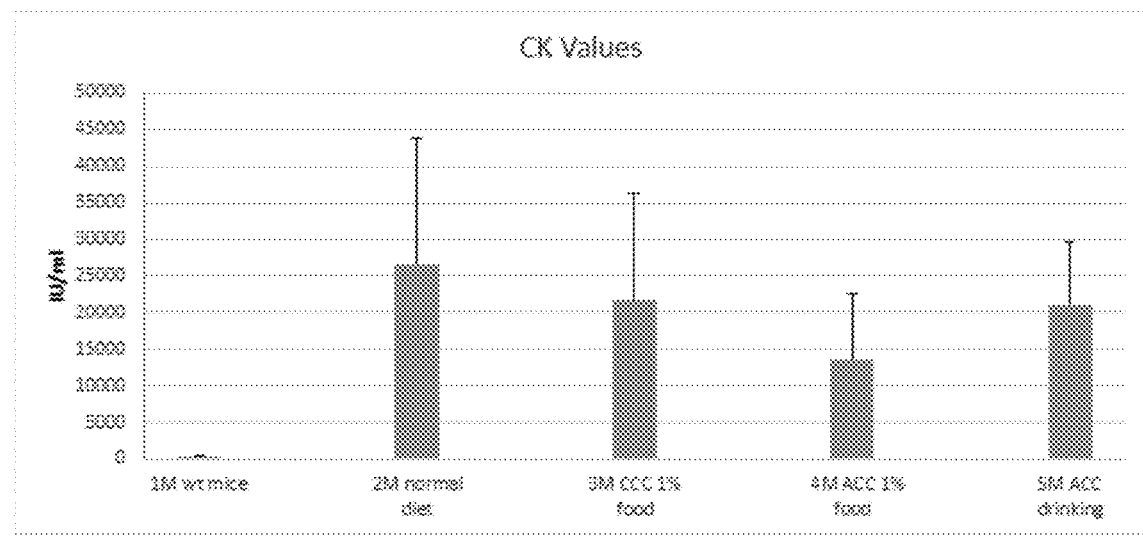
FIG. 8 shows the creatinine kinase values of mice (wild type and mdx mice) administrated orally with different types of calcium supplements.

The result of Creatinine Kinase test is shown in FIG. 8 and demonstrate a clear trend. All mdx mice showed elevated values of CK vs. the wild type, which indicates on muscle destruction. However, the elevation was significantly more moderate in the group that received ACC by food (4M group) compared to the group that received normal diet only (2M group; student's t-test, P value=0.034). While the mice in group 3M that received CCC also showed a more moderation elevation in the CK levels in comparison to mice of group 2M (no treatment), the difference was not statistically significant (student's t-test, P value=0.45).

Group 5M that received ACC by drinking demonstrated results similar to those of group 3M that received CCC by food (21,164±8,391 and 21,676±14,508 IU/ml, respectively). Without wishing to be bound by any theory or mechanism of action it is suggested that the reason for the difference in the results between the groups 4M (ACC in food) and 5M (ACC by drinking) may be due to heterogeneity of the ACC suspension and therefore non uniform administration of the ACC. It is clear though, that administration of ACC significantly alleviated the symptoms of DMD in the mdx mice.

Example 7—Evaluating the Effect of ACC Consumption on Muscle Dystrophy in MDX Mice In the present example, the effect of ACC stabilized by different stabilizers on mdx mice (rodent model of Duchenne Muscular Dystrophy) was tested.

Test Articles

Mice were administrated with stabilized ACC orally (feeding) every day or by IP injections, consecutive, six times a week. The control or test Items were administered similarly.

Test System:
Species: Mice
Mdx Strain: C57/Bl 10 ScSn/DMD mdx/J
Wild type Strain: C57BL/6JOIaHsd.
Gender & Age: Males, 3-5 weeks of age at study initiation
Body Weight: Weight variation of animals at study initiation should not exceed ±15% % of the mean weight of the gender.
Group Size: see Table 1, study design
No. of Groups: 6 (see Table 6)

TABLE 6

Study Design

| Group No. | Strain | n= | Group Name and Treatment Details | Route of Administration | Duration |
|---|---|---|---|---|---|
| 1M | C57BL-Rodent | 6 | Wild type control-commercial diet (Teklad) | Feeding | 24 weeks |
| 2M | MDX-Rodent | 8 | Mdx control-commercial diet | | |
| 4M | | 10 | ACC stabilized by PS-Low Calcium Diet (TDK95027, Harlan Inc.) containing 1% elemental calcium from synthetic ACC (5% PS) ad libitum | | |
| 3M | | 10 | ACC stabilized by TP-Low Calcium Diet (TDK95027, Harlan Inc.) containing 1% elemental calcium from synthetic ACC (6% TP-2% Citric Acid) ad libitum | | |
| 5M | | 10 | ACC stabilized by TP-200 µl containing 0.1% elemental calcium from synthetic ACC (10% TP) Injections are be performed 6 consecutive times a week | Intra-peritoneal (IP) injection | 12 weeks |
| 6M | | 6 | Control-saline control-200 µl containing Saline. Vehicle Injections are performed 6 consecutive times a week | | |

PS—Phosphoserine;
TP—Triphosphate

Experimental Procedure:

The MDX mouse is an animal model for evaluating the Duchenne Muscular Dystrophy (DMD).

Study end Definition: Study is terminated 24 weeks from beginning for groups 1-4 and 12 weeks from beginning for groups 5-6.

Test Items Administrations

All animals (except for control) were administrated with stabilized ACC either by food (every day) or by IP injections (six consecutive times a week).

Tests and Evaluations

Clinical Signs Observation

The animals were observed for clinical signs once a week until study termination.

Observations was performed for any changes in skin, fur, eyes, mucous membranes, respiratory, occurrence of secretions and excretions (e.g. diarrhea). Changes in gait, posture and response to handling, as the presence of bizarre behavior, tremors, convulsions, sleep and coma were also included.

All observed abnormalities, toxic signs, moribund condition and pre-terminal deaths were recorded.

Animals that were humanely sacrificed during the test are considered for the interpretation of test results as animals that died during the test.

Body Weight Measurements

Body weight measurements was recorded once a week, shortly before the four limb hanging test. At study beginning and termination body weight was also measured.

Functional Test—Four Limb Hanging Tests (Grip Test)

Four limb hanging test was used to monitor muscle strength and to indicates on neuromuscular impairment and motor coordination. The test was used to determine the efficacy of ACC.

In the four limb hanging test a wire grid system is used to measure the ability of mice to exhibit sustained limb tension oppose their gravitational force. The hanging time is measured in seconds as well as the minimal Holding impulse (Holding impulse=Body mass×Hang time, [N sec], conversion factor−9.806×$10^3$ Newton/gr).

Grip Test (four limb hanging test) was performed according to the TREAT-NMD SOP #DMD_M.2.1.005 protocol. Briefly:

Mouse (min age—4 weeks) was placed on a top of a grid (grid square size about 1×1 $cm^2$) and was allowed to accommodate to this environment 3-5 seconds.

Grid was flipped over such that the mouse is upside down. The grid height was placed at least 35 cm above the cage floor. Sufficient amount of soft bedding (5-7 cm) was placed under the grid to ensure soft landing. Mice at the age of 4-24 weeks naturally try to stay on grid and avoid falling to the ground. This height is low enough not to injure the animal, and high enough to ensure avoidance of fall.

Each hang period must begin with all 4 mouse paws grasping the grid. Hanging time was measured by a stopwatch and recorded.

The test performed up to a max of 600 sec or repeated 3 times with a rest interval of at least 2 minutes.

The longest Hanging time was used to assess the Holding impulse.

Four limb hanging test was done each week during the whole experiment.

Blood Collection and Serum Preparation for Creatinine Kinase (CK) Levels:

At study termination blood samples are drawn from the all animals under light anesthesia (with Ketmaine/Xylazine) directly from the retro orbital sinus.

200 μl blood is collected into a yellow-cup tube with clotting activator gel. The tubes are kept at room temperature for at least 30 minutes for clotting and centrifuged at room temperature for 10 minutes at 4000 RPM. The serum samples will be stored at 2-4° C. until delivered to CK analysis at A.M.L labs.

Study Termination and Necropsy

Following terminal bleeding, animals is sacrificed by Carbon dioxide asphyxiation and gross pathology is performed examining the major tissues and organ systems.

Skeletal Muscles Collection

During the necropsy, selected muscles (diaphragm, cardiac and gastrocnemius) from all animals are collected. Muscles from all animals are preserved in 10% neutral buffered formalin (approximately 4% formaldehyde solution) for at least 24 hours for future histopathology.

Results

Mice in all groups gained weight. No significant difference was found in the average body weight in any of the groups.

Functional Test—Four Limb Hanging Test—Intermediate Results

Figure 9:
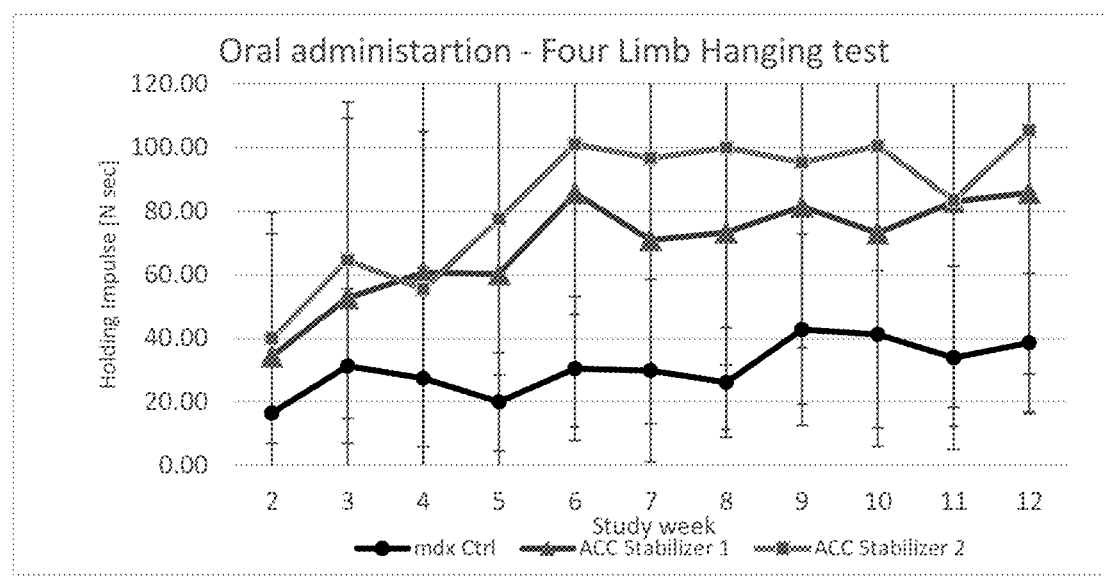
FIG. 9 shows the effect of administration of stabilized ACC mdx mice on their performance in Four limb hanging test.

A significant difference was found in the Holding impulses (HI) of both mdx groups that were administrated orally with ACC formulations (stabilizer 1—phosphoserine, stabilizer 2-triphosphate) versus the control group that was administrated with standard diet (comprising calcium), see FIG. 9. The difference was observed already on the second week of the study where the HI of ACC treated mice was 2 time higher that the HI of the control group. This differences increase as the study progressed and reached a plateau after about 6-8 weeks. It can be seen from FIG. 9 that the HI of ACC treated mice was about ×2-×3.8 times higher than of the control group.

Example 8. Enhancement of Embryonic Development in ACC Supplemented Media

Materials and Methods

CBA male mice were bred with BL C57 female mice. The mice were kept on a 12 hours photoperiod schedule with unlimited water and food supply. About 6 to 8 weeks after receiving offspring, each female mouse was injected IP with 5 IU of pregnant mare serum gonadotropin (PMSG).

After 48 hours each female mouse was injected IP with 5 IU human chorionic gonadotropin (hCG). Male mice proven to be fertile were then put together with the superovulated females. The next morning the female mice were examined for the presence of copulatory plugs. Females that had copulatory plugs were euthanized after 24 hours (approximately 36 hours post-coitus) and embryos at 2 cell stage were retrieved from the oviducts as following: the oviducts were dissected in Quinn's Advantage cleavage media (SAGE, Origio, Denmark) and the embryos were transferred to 20 μL drops with Quinn's Advantage cleavage media (SAGE, Origio, Denmark) overlaid with mineral oil and cultured at 37.0° C. under 5% $CO_2$ and atmospheric oxygen. The collected embryos continued to grow, i.e. in-vitro culture (IVC), until blastocyst/hatching stage. To test the effect of amorphous calcium carbonate, the Quinn's Advantage cleavage media ("cleavage media" hereinafter) was supplemented with different additives, i.e. amorphous calcium carbonate stabilized by polyphosphate (ACC-PP), crystalline calcium carbonate (CCC), polyphosphate (PP), phosphoserine (PS) or sodium carbonate ($NaCO_3$). All supplements were added as a freshly prepared suspension; the preparation of the ACC supplements were performed under aseptic conditions. Untreated cleavage media (without addition of any additive) was used as a control (identified as Cont Q). The embryos were evaluated every day by microscope observation for a detection of the following stages: 2 cells, compactions stage, blastocysts formation and hatching stage. The fraction (in percent) of the embryos reached each stage was calculated (the number of 2 cells embryos was set as 100%).

Results

Embryos development in the cleavage media supplemented with 1.7 mM of amorphous calcium carbonate stabilized with PP (ACC-PP) was compared to a control (Cont Q—development in untreated media). The number of embryos at each developmental stage and their portion of the initial number of embryos (the latter is presented in parentheses) are presented in Table 7.

TABLE 7

Comparison between the embryos grown in the untreated cleavage media and media supplemented with ACC-PP

|  | 2 Cell/d1 | Comp/d2 | Blast/d3 | Hatch/d4 |
|---|---|---|---|---|
| Cont Q | 12 | 2 (16.6) | 10 (83.3) | 8 (66.6) |
| ACC-PP | 40 | 17 (42.5) | 40 (100) | 32 (80) |

Example 9

Embryo development in the cleavage media supplemented with 1.7 mM of either ACC-PP or calcium chloride ($CaCl_2$)) was tested in two separate tests (A and B). In Test A the embryos were grown until the blastocyst stage and in Test B, until the hatching stage. The number of embryos at each developmental stage and their portion of the initial number of embryos (in parentheses) are presented in Table 8 (Test A) or Table 9 (Test B).

TABLE 8

Test A: comparison between embryos grown in cleavage media supplemented with 1.7 mM of either $CaCl_2$ or ACC-PP

|  | 2 Cell/d1 | Comp/d2 | Blast/d3 |
|---|---|---|---|
| $CaCl_2$ | 25 | 16 (64) | 16 (64) |
| ACC-PP | 26 | 24 (92.3) | 22 (84.6) |

TABLE 9

Test B: comparison between embryos grown in cleavage media supplemented with 1.7 mM of either CaCl2 or ACC-PP

|  | 2 Cell/d1 | Comp/d2 | Blast/d3 | Hatch/d4 |
|---|---|---|---|---|
| $CaCl_2$ | 27 | 20 (70) | 20 (74) | 11 (40.7) |
| ACC | 23 | 23 (100) | 23 (100) | 23 (100) |

Example 10

Embryo development in the cleavage media supplemented with 1.7 mM $CaCl_2$, 1.7 mM ACC-PP or 0.85 mM ACC-PP (half of the initial concentration of ACC-PP, identified as ACC-PP0.85). The number of embryos at each developmental stage and their portion of the initial number of embryos (in parentheses) are presented in Table 10.

TABLE 10

Comparison between embryos grown in cleavage media supplemented with 1.7 mM $CaCl_2$, 1.7 mM or 0.85 mM ACC-PP.

|  | 2 Cell/d1 | Comp/d2 | Blast/d3 | Hatch/d4 |
|---|---|---|---|---|
| $CaCl_2$ | 10 | 3 (30) | 8 (80) | 3 (30) |
| ACC | 11 | 7 (63.6) | 9 (81.8) | 7 (63.6) |
| ACC-PP0.85 | 11 | 8 (72.7) | 9 (81.8) | 8 (72.7) |

Example 11

Embryos development in the cleavage media supplemented with 1.7 mM $CaCl_2$, 1.7 mM or 0.85 mM ACC-PP (ACC-PP0.85) were tested and compared to the development in the untreated media. The number of embryos at each developmental stage and their portion of the initial number of embryos (in parentheses) are presented in Table 11.

TABLE 11

Comparison between embryos grown in the untreated cleavage media and media supplemented with 1.7 mM $CaCl_2$, 1.7 mM or 0.85 mM ACC-PP.

|  | 2 Cell/d1 | Comp/d2 | Blast/d3 | Hatch/d4 |
|---|---|---|---|---|
| Cont Q | 42 | 30 (71.4) | 38 (90.4) | 15 (35.7) |
| $CaCl_2$ | 30 | 16 (53.3) | 24 (80) | 13 (43.3) |
| ACC-PP | 30 | 23 (76.6) | 27 (90) | 12 (40) |
| ACC-PP0.85 | 30 | 21 (70) | 30 (100) | 24 (80) |

Example 12

In this experiment 4 female mice aged 5 months old were euthanized. The embryos from each mouse were collected as described in materials and methods, however the embryos were not pooled together the embryos from each oviduct of each mice were either grown in the cleavage media supplemented with 1.7 mM $CaCl_2$) or 1.7 mM ACC-PP grown separately in the culture. This way we could also evaluate the differences between the mice since the embryos from each female were siblings. The number of embryos at each developmental stage and their portion of the initial number of embryos (in parentheses) are presented in Table 12.

TABLE 12

Comparison between embryos from 4 female mice grown separately in cleavage media supplemented with 1.7 mM of either $CaCl_2$ or ACC-PP.

| Mouse # | $CaCl_2$ Total embr. | ACC-PP Total embr. | $CaCl_2$ 2Cell/d1 | $CaCl_2$ irreg/d1 | ACC-PP 2Cell/d1 | ACC-PP irreg/d1 | $CaCl_2$ 8Cell/d2 | $CaCl_2$ comp/d2 | ACC-PP 8Cell/d2 | ACC-PP comp/d2 | $CaCl_2$ Blast/d3 | ACC-PP Blast/d3 | $CaCl_2$ Hatch/d4 | ACC-PP Hatch/d4 |
|---|---|---|---|---|---|---|---|---|---|---|---|---|---|---|
| 1 | 12 | 11 | 3 | 9 | 3 | 8 | 2 | 1 | 0 | 3 | 1 (8.3) | 3 (27.3) | 0 (0) | 2 (18.2) |
| 2 | 9 | 13 | 3 | 6 | 4 | 9 | 0 | 3 | 0 | 5 | 2 (22.2) | 5 (38.5) | 0 (0) | 4 (30.8) |
| 3 | 10 | 10 | 7 | 3 | 3 | 7 | 0 | 6 | 0 | 4 | 5 (50) | 4 (40) | 3 (30) | 3 (30) |
| 4 | 18 | 17 | 14 | 4 | 13 | 4 | 4 | 10 | 2 | 12 | 12 (66.7) | 14 (82.3) | 7 (41.2) | 12 (70.6) |

Example 13

In this experiment, 7 female mice aged 6 months old were euthanized. From each mouse the embryos were collected as described in materials and methods, however from mouse no. 1 and 2 the embryos were not pooled together but rather grown separately, as in Example 5. The embryos from mouse no. 1 were either grown in untreated cleavage media or medium supplemented with 2.6 mM ACC-PP (ACC-PP2.6). The embryos from mouse no. 2 were grown in the cleavage media supplemented with 1.3 mM or 0.6 mM of ACC-PP (identified as ACC-PP 1.3 and ACC-PP0.6, respectively). Embryos from mice no. 3-7 all were pooled together and grown with 1.6 mM of polyphosphate (PP). In addition, the diameters and volumes of the blastocysts were calculated. The number of embryos at each developmental stage and their portion of the initial number of embryos (in parentheses) are presented in Table 13.

TABLE 13

Comparison between sibling embryos grown in untreated cleavage media or media supplemented with ACC-PP at different concentrations. The pooled embryos from mice No. 3-7 were grown in the media supplemented with polyphosphate.

|  | Mouse 1 | | Mouse 2 | | |
| --- | --- | --- | --- | --- | --- |
| Additive | Cont Q | ACC-PP2.6 | ACC-PP1.3 | ACC-PP0.6 | Mice 3-7 PP |
| Total # | 17 | 19 | 18 | 13 | 37 |
| 8 cell/d2 | 7 | 3 | 7 | 4 | 9 |
| comp/d2 | 10 | 16 | 11 | 8 | 20 |
| Blast/d3 | 17 (100) | 19 (100) | 18 (100) | 13 (100) | 20 (54.1) |
| Hatch/d4 | 11 (64.7) | 19 (100) | 17 (94.4) | 6 (46.2) | 17 (45.9) |

It was found that the hatched blastocysts that were grown with 2.6 mM of ACC-PP had 28% bigger diameter and 2 times bigger volume than the control.

Example 14

In this experiment, 7 female mice aged 6 months old were euthanized. The embryos from each mouse were collected as described in materials and methods (Example 6). The embryos were pooled together and divided into 5 groups that were grown in the untreated cleavage medium (Cont Q), or in the medium supplemented with 2.6 mM, 1.3 mM, 0.6 mM ACC-PP (identified as ACC-PP2.6, ACC-PP1.3 and ACC-PP0.6, respectively), or 1.6 mM of polyphosphate (PP). The number of embryos at each developmental stage and their portion of the initial number of embryos (in parentheses) are presented in Table 14.

TABLE 14

Comparison between the embryos grown in the untreated cleavage media or media supplemented with 2.6 mM, 1.3 mM or 0.6 mM ACC-PP or with 1.6 mM PP.

|  | Cont Q | ACC-PP2.6 | ACC-PP1.3 | ACC-PP0.6 | PP |
| --- | --- | --- | --- | --- | --- |
| Total # | 42 | 20 | 31 | 21 | 36 |
| 8 cell/d2 | 19 | 5 | 7 | 5 | 6 |
| comp/d2 | 25 | 15 | 24 | 16 | 30 |
| Blast/d3 | 35 (83.33) | 20 (100) | 26 (83.87) | 3 (14.28) | 34 (94.44) |
| Hatch/d4 | 16 (38.09) | 19 (95) | 15 (48.38) | 18 (85.7) | 16 (44.44) |

Example 15

In this experiment, 6 female mice aged 6 months old were euthanized. The embryos from each mouse were collected as described in materials and methods. The embryos were pooled together and were divided into 3 groups: one served as control (Cont Q), and in two other groups the embryos were grown in the cleavage media supplemented with 3.3 mM of ACC-PP (ACC-PP3.3) or with 3.3 mM of commercially available nanometric crystalline calcium carbonate (CCC). All the three media were prepared under aseptic conditions. The number of embryos at each developmental stage and their portion of the initial number of embryos (in parentheses) are presented in Table 15.

TABLE 15

Comparison between the embryos grown in the untreated cleavage media or media supplemented 3.3 mM ACC-PP or 3.3 mM CCC.

|  | Cont Q | ACC-PP 3.3 | CCC |
| --- | --- | --- | --- |
| Total # | 18 | 45 | 17 |
| 8 cell/d2 | 10 | 0 | 3 |
| comp/d2 | 8 | 45 | 14 |
| Blast/d3 | 18 (100) | 45 (100) | 17 (100) |
| Hatch/d4 | 14 (77.7) | 42 (93.3) | 14 (82.35) |

Example 16

In this experiment, 6 female mice aged 7 months old were euthanized. From each mouse the embryos were collected as described in materials and methods (Example 6). The embryos were pooled together and were grown in the cleavage media supplemented with 1.7 mM $CaCl_2$, 1.7 mM ACC-PP, 0.8 mM of ACC-PP (ACC-PP0.8) or 1.7 mM of phosphoserine (PS). The number of embryos at each developmental stage and their portion of the initial number of embryos (in parentheses) are presented in Table 16.

TABLE 16

Comparison between the embryos grown in the cleavage medium supplemented with 1.7 mM $CaCl_2$, 1.7 mM, 0.8 mM ACC-PP or 1.7 mM of PS.

|  | $CaCl_2$ | ACC-PP | ACC-PP 0.8 | PS |
| --- | --- | --- | --- | --- |
| Total # | 11 | 15 | 14 | 13 |
| 8 cell/d2 | 6 | 1 | 3 | 5 |
| comp/d2 | 5 | 14 | 11 | 8 |
| Blast/d3 | 10 (90.90) | 14 (93.3) | 14 (100) | 12 (92.3) |
| Hatch/d4 | 4 (36.36) | 13 (86.6) | 11 (78.57) | 10 (76.9) |

It can be seen that in that particular experiment adding calcium chloride had a negative effect on embryonic development resulting in a lower percentages of blastocysts and hatched blastocysts.

Example 17

In this experiment 6 female mice aged 6 months old were euthanized. The embryos from each mouse were collected as described in materials and methods (Example 6), however the embryos from mouse no. 1 and 2 were not pooled together but rather grown separately as a sibling experiment (see Example 10). The embryos from female no. 1 were grown in the untreated cleavage media or in the media supplemented with 1.7 mM nanometric crystalline calcium carbonate (CCC). The embryos from mouse no. 2 were grown in the media supplemented with 1.7 mM ACC-PP or with 1.7 mM of sodium carbonate (NaCO$_3$). All the embryos from mice no. 3-6 were pooled together and grown in the untreated media or media supplemented with 1.7 mM NaCO$_3$ or 1.7 mM ACC-PP. In addition, the diameter and volume of the blastocysts were calculated (see Table 17).

TABLE 17

A development assessment of sibling embryos taken from two mice and of pooled embryos grown in differently supplemented cleavage media.

|  | Mouse 1 | | Mouse 2 | | Mice 3-6 | | |
|---|---|---|---|---|---|---|---|
| Additive | Cont Q | CCC | ACC-PP | NaCO$_3$ | Cont Q | NaCO$_3$ | ACC-PP |
| Total # | 20 | 24 | 12 | 16 | 20 | 10 | 19 |
| 8 cell/d2 | 14 | 14 | 3 | 6 | 14 | 2 | 17 |
| comp/d2 | 6 | 6 | 8 | 8 | 6 | 7 | 8 |
| degenerative | 0 | 1 | 1 | 2 | 0 | 1 | 0 |
| early Blast/d3 | 11 | 8 | 2 | 14 | 12 | 0 | 2 |
| Blast/d3 | 9 | 12 | 9 | 2 | 8 | 0 | 17 |
| Blast/d4 | 6 | 5 | 0 | 0 | 6 | 0 | 0 |
| Hatch/d4 | 14 | 15 | 11 | 2 | 14 | 0 | 19 |
|  | (70) | (62.5) | (91.6) | (12.5) | (70) | (0) | (100) |

It can be seen that adding sodium carbonate resulted with very poor embryonic development compared to control or to the addition of ACC-PP. It was also found that the hutched embryos that were grown in the media cleavage media substituted with 2.6 mM of ACC-PP had a 28% bigger diameter and ×2 times a bigger volume than the control.

Example 18. Preparation of 10% TP-1% Citric Acid ACC (ACC Stabilized with 10% Triphosphate and 1% Citric Acid) Formulated as Cell Culture Medium Supplement 36 ml of 3% Calcium chloride solution were mixed with 4 ml of 0.27% Citric Acid solution and with 10 ml of 0.5406% Triphosphate solution. Then 40 ml of 1.9485% Sodium carbonate solution was added to precipitate ACC. 10 ml of the stabilizing solution containing 0.5406% triphosphate was added to the ACC suspension creating stabilized ACC suspension. The obtained suspension was used as a supplement to Quinn's™ cleavage medium or to Quinn's™ 1-Step medium. The suspension was added to the final concentration of ACC of 1.7 or 3.4 mM. Alternatively, the suspension is filtered using a Buchner funnel, the cake is washed with water and the cake is further dried, e.g. in the oven. The powder is added to the cleavage medium to the final concentration of 1.7 or 3.4 mM.

Example 19

Figure 10:
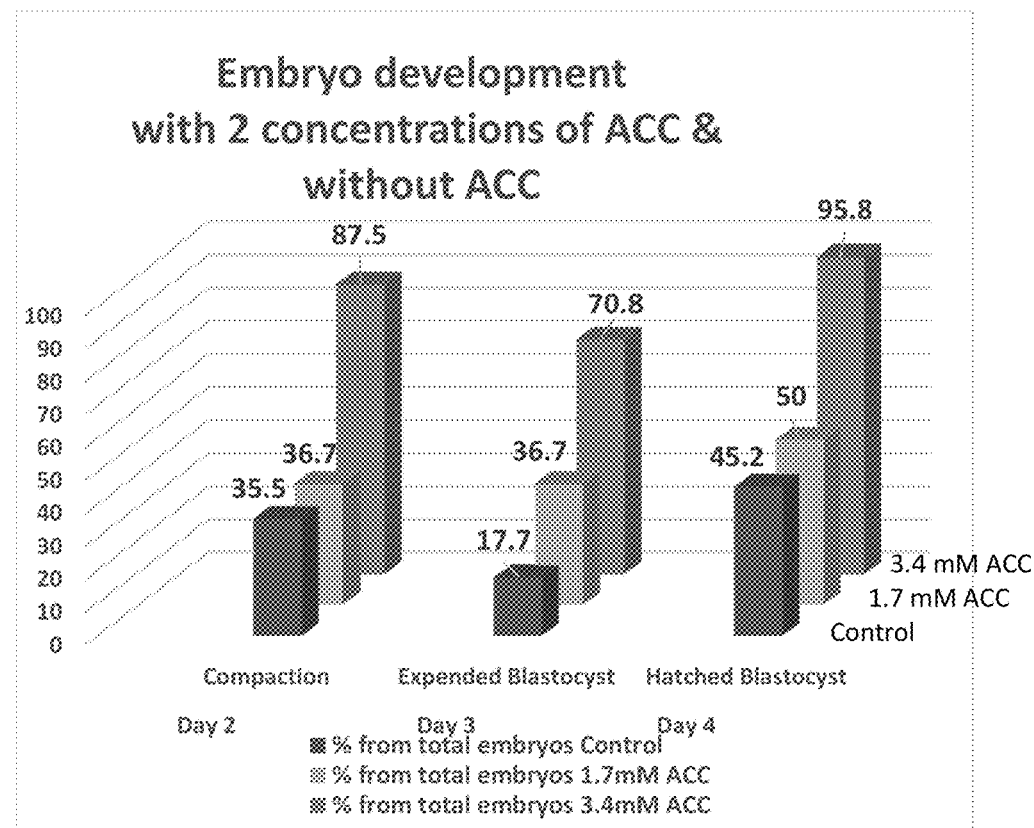
FIG. 10 shows the effect of stabilized ACC on mice embryos development in vitro in one step medium with different concentration of ACC.

In this experiment 4 female mice aged 6-8 weeks old were euthanized. The embryos from each mouse were collected as described in materials and methods. The stabilized ACC (ACC stabilized with 10% triphosphate and 1% citric acid) was prepared as described in Example 16. The embryos from each female were separated and were grown one part in the untreated SAGE 1-Step™ medium and the second part in the SAGE 1-Step™ medium supplemented with 1.7 mM ACC-PP or 3.4 mM ACC-PP. As can be seen from FIG. 10 addition of stabilized ACC had a positive effect on the embryonic development resulting in a higher percentages of blastocysts and hatched blastocysts especially with the 3.4 mM ACC. Unexpectedly, no transfer to any other media was required for increasing the rate of hatched blastocytes.

Example 20

Figure 11:
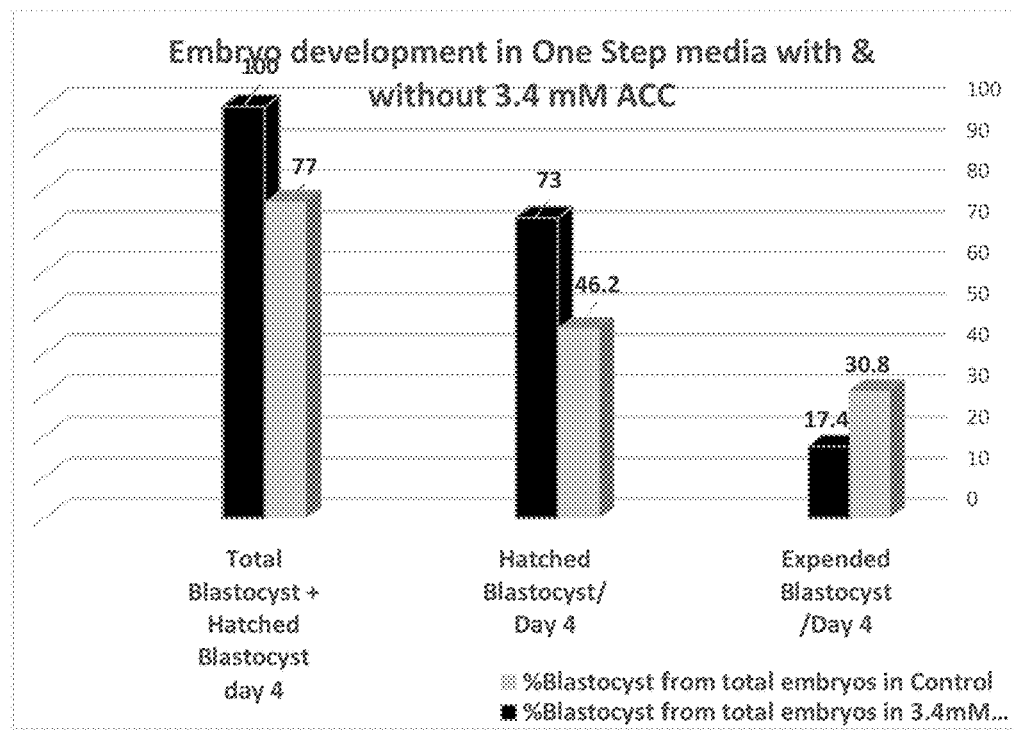
FIG. 11 shows the effect of stabilized ACC on mice embryos development in vitro in one-step medium.

In two different experiments, 3 female mice aged 6-8 weeks old were euthanized (in each experiment). The embryos from each mouse were collected as described in materials and methods. The stabilized ACC (ACC stabilized with 10% triphosphate and 1% citric acid) was prepared as described in Example 17. In one experiment (experiment A), the embryos from each female were separated and were grown one part in the untreated SAGE 1-Step™ medium and the second part in the SAGE 1-Step™ medium supplemented with 3.4 mM ACC-PP. In the second experiment (experiment B), the embryos from each female were separated and were grown one part in the untreated Cleavage medium (SAGE) and the second part in the Cleavage medium supplemented with 3.4 mM ACC-PP. Results of these experiments are presented in FIG. 11 (experiment A) and FIG. 12 (experiment B).

As can be seen from the experiments addition of stabilized ACC had a positive effect on the embryonic development resulting in a higher percentages of blastocysts and hatched blastocysts especially. Unexpectedly, no transfer to any other media was required for increasing the rate of hatched blastocytes for both media.

Example 21. Preparation of ACC Formulated as Cell Culture Medium Supplement

Compositions of ACC stabilized by different stabilizers (triphosphate (TP), hexametaphosphate (HMP), pyrophosphate (Pyr), phosphoserine (PS), Etidronic acid (ET), Zoledronic acid (ZA); or Medronic acid (MA) were prepared) were prepared. In a typical procedure, a calcium solutions (300 ml of water, 24 g of calcium chloride and a stabilizer) and a carbonate solution (200 ml of water and 17.3 g of sodium carbonate) were mixed together to precipitate ACC. A stabilizer solution (100 ml of water and stabilizer; the content of the stabilizers in the calcium and stabilizer solution is presented in Table 18) was added to the ACC suspension creating stabilized ACC suspension. The suspension may be used as a supplement. The ACC was then filtered using a Buchner funnel, and the cake was washed with water. The suspension was dried to obtain a powder. The powder may be added as a cell culture medium supplement or resuspended in an aqueous medium and added as a suspension.

TABLE 18

The content of the stabilizers in different ACC composition

| Stabilizer in: | 1% TP | 2% TP/ HMP/Pyr | 3% TP/ HMP/Pyr | 4% TP/ HMP/Pyr | 5% TP/HMP/Pyr/ PS/ET/ZA/MA | 6% TP/HMP/ Pyr/PS/ | 10% TP/HMP/Pyr/ PS/ET/ZA/MA | 15% TP/HMP/ Pyr/PS |
|---|---|---|---|---|---|---|---|---|
| Calcium solution (g) | 0.12 | 0.24 | 0.36 | 0.48 | 0.6 | .072 | 1.2 | 1.8 |
| Stabilizing solution (g) | 0.12 | 0.24 | 0.36 | 0.48 | 0.6 | .072 | 1.2 | 1.8 |

In other examples the compositions were prepared as described above, with addition of citric acid to calcium solutions so as to obtain 1% citric acid in the final composition. The suspension is used per se as a culture medium supplement. Alternatively, the suspension was further washed with water and dried so as to obtain a powder. The powder may be added to any cell culture medium or be resuspended in aqueous medium.

Example 22. Growth of MBA13 Stem Cells (Bone Marrow Stromal Cells) to Osteoblasts Material and Methods Two days following thawing, MBA-13 cells (received from Prof. Dov Zipori, Weizmann Institute of Science) were re-suspended in recombinant trypsin solution and seeded on a 96 wells plate, (Day "0") in a concentration of $1 \times 10^4$ cells/well using MSC Nutristem® XF basal medium (Biological Industries, cat #05-200-1A) supplemented with Mesenchymal stem cells (MSC) supplement mix medium (Biological Industries cat #05-201-06) in a ratio of 50 ml:300 µl. Rows A-H of columns 1-4 of the 96 plate were pre-coated with MCS attachment solution diluted in PBS (without $Ca^{2+}$, $Mg^{2+}$), in a ratio of 1:100 for cells seeding. Rows A-H of Columns 5-8 of the 96 plate were pre-coated with Gelatin 0.1% for 30 minutes at room temperature.

On day 2, when more than 80% cell confluence was achieved (~48 h) the medium was changed to MSCgo rapid osteogenic medium (cat #05-442-1B) containing factors that promote osteoblastic differentiation. Following medium change, rows A-C were supplemented with additional 1 mM calcium (total 2.488 mM calcium) originated from Amorphous Calcium Carbonate (ACC) stabilized by 10% Triphosphate+1% citric acid; rows D-F were supplemented with additional 1 mM calcium (total 2.488 mM calcium) originated from calcium chloride; Row G in the plate was treated with MSCgo medium (total 1.488 mM calcium). Row H of the plate was treated with MSC NutriStem® XF nutrient basal medium+supplement mix (total 1.488 mM calcium).

On day 4, medium was exchanged with fresh preparations of ACC.

In parallel, a control plate was also seeded with MDX cell lines originated from damaged muscles of MDX mice. The staining of these cell was used to set the background staining of cells intrinsic calcium and also to eliminate the possibility that calcium deposition of the ACC treatment is stained. Prior seeding, wells were coated with gelatin, which is used as a standard substrate for MDX cells attachment. MDX Cells were seeded on a 24 well plate in a concentration of $3 \times 10^4$ cells/well. Seeding day is defined as "Day 0".

On day 2, the medium in the wells was replaced with the following:

Columns 1 and 2 were treated with Spinal Cord (SC) medium that is prepared in-house (the medium comprises 0.6 wt % D-glucose, 2 mM L-glutamine, Gentamicin 25 µg/ml, B27, $N_2$, BSA 0.1 mg/ml, Hepes, 10% FBS, DMEM/F12 and IGF-I, 50 ng/ml)+1 mM calcium originated from ACC (total calcium concentration of 2 mM); columns 3 and 4 were treated with SC medium+1 mM originated from $CaCl_2$); Columns 5 and 6 were treated with SC medium. Both types of cells (MBA13 and MDX) were cultured up to 10 days.

Fixation (with 4% Paraformaldehyde for 20 minutes) of few wells from each type was performed on the 5th, 7th and 10th day following medium exchange, that are Days 7, 9 and 12 of the study.

Once the cells were fixated, two types of staining reagents were used to stain extracellular calcium or bone deposition in order to evaluate osteoblasts functionality: (i) Alizarin red (Sigma A55333) and (ii) Alkaline Phosphatase (DAKO BCIP/NBT substrate system K0598) as following:

Alizarin red staining procedure—pH was adjusted to 4.2. Cells were washed twice with PBS and fixed with cold methanol for 5 minutes and then washed again with PBS. Alizarin solution in a concentration of 2% was used for 15-20 minutes. Following staining incubation, the samples were washed with water 2-3 times to remove unspecific staining.

Alkaline Phosphatase staining—cells were washed 1 or 2 times with PBS and then fixed with 4% paraformaldehyde for 20 min. Then, washed 3 times with PBS and following removal of PBS remnants, 3 drops of BCIP/NBT kit solution was used to cover the cells including one empty well without any cells as control to quantify the assay. Incubation of the Alkaline phosphatase kit was performed for 1 hour and then rinsed with distilled water.

Results

The results of cells that were cultured for 10 days and stained by both Alizarin and Alkaline phosphatase are provided. Observation performed prior to 10 days hardly detected any calcium deposition in both staining methods.

Cells condition was observed under a light microscope (without fixation) at two time points, days 2 and 4. On both observations, cells that were seeded on wells pre-coated with MSC attachment solution were not in a good condition; the cells became rounded. In contrast, cells that were seeded on wells pre-coated with gelatin were in a good condition. Nevertheless, it was decided to continue with both types of pre-coating. The following results and staining procedures refers to cells grown in Gelatin that was used as attachment substrate.

In Alizarin Red staining, calcium deposits are detected by an orange red color.

Figure 13:
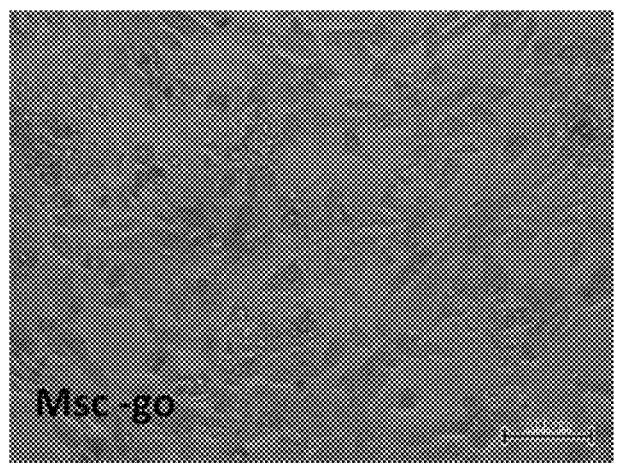
FIGS. 13A-13C shows Alizarin red staining of osteoblasts following 10 days in culture as a function of various medium treatments. The media was supplemented with additional 1 mM $Ca^{2+}$ from: A—ACC, B—$CaCl_2$, or C—control, no $Ca^{2+}$ addition.

Alizarin Red staining demonstrated a very strong signal in osteoblast cell samples that were supplemented with ACC compared to those supplemented with $CaCl_2$, which demonstrated a weak signal only, (FIG. 13). In addition to the signal, it can be seen in the figure that large plaques of calcium deposition are stained which are not observed in any of the controls treatments.

The Alizarin Red staining of cells grown in MSCgo rapid medium also demonstrated some staining of calcium deposition but the size of the deposition and its amount is significantly lower, and resembles the morphology and amount observed for cells supplemented within $CaCl_2$. Calcium deposition was not seen at cells grown in MSC NutriStem® XF supplements (MSC sup; data not shown). MSC NutriStem® XF sup medium is normally used to induce cells proliferation rather than differentiation. Indeed the number of cells observed is large but no calcium deposition is observed.

This observation suggests that ACC treatment enhances MBA13 cells differentiation into osteoblasts and raises the cells calcium deposition, i.e. enhances their functionality.

Another independent marker for osteoblast differentiation is the alkaline phosphatase. This enzyme is expressed maximally when the matrix maturation phase of cells occurs. Alkaline phosphatase staining was used as a complementary method to detect osteoblasts differentiation and functionality so as to verify the result obtained by the Alizarin staining.

Figure 14:
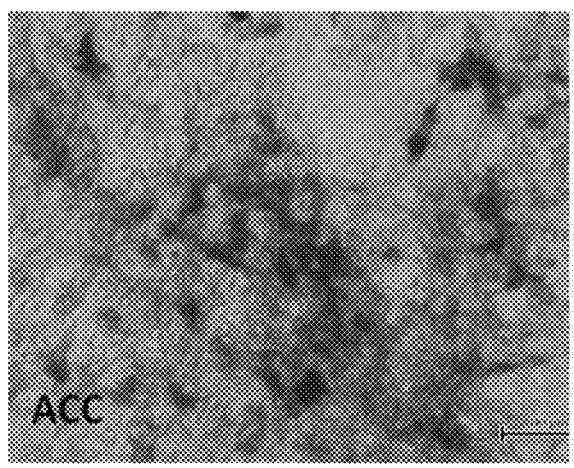
FIGS. 14A-14C shows Alkaline phosphatase staining of osteoblasts following 10 days in culture as a function of various medium treatments. The media was supplemented with additional 1 mM $Ca^{2+}$ from: A—ACC, B—$CaCl_2$, or C—control, no $Ca^{2+}$ addition.
Figure 14:
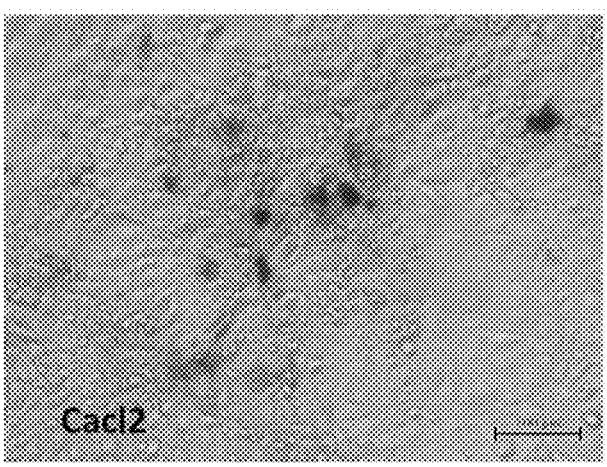
Figure 14:
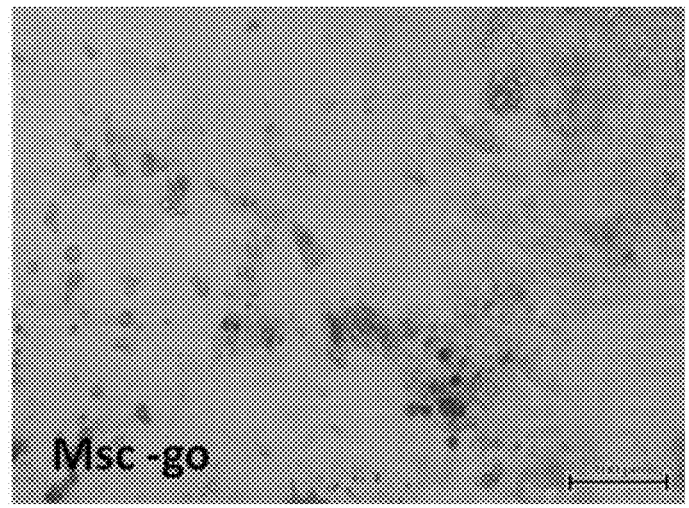

The alkaline phosphatase staining is shown in black color and the results are presented on FIG. 14. MBA13 cells that were treated with ACC demonstrated an intense signal in comparison to the other treatments. Indeed, Alkaline phosphatase staining support that osteoblasts differentiation is better in cultures treated with ACC.

Figure 15:
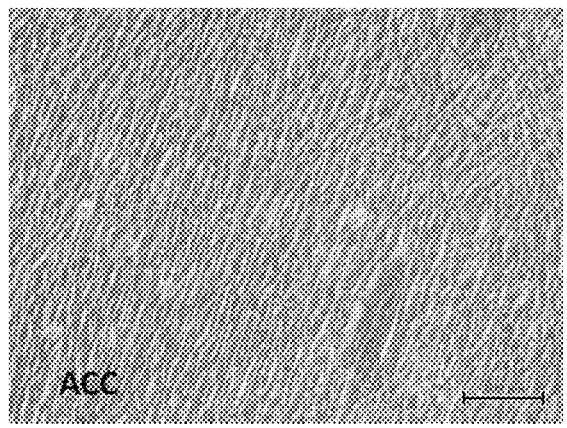
FIGS. 15A-15F shows Alizarin red staining (A-C) and Alkaline phosphatase (D-F) of mdx cell lines grown in media with different sources of additional 1 mM $Ca^{2+}$ added: A and D—ACC, B and E—$CaCl_2$, or C and F—control, no $Ca^{2+}$ addition.
Figure 15:
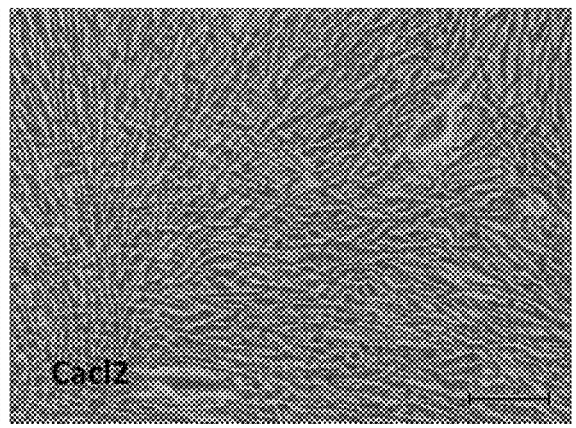
Figure 15:
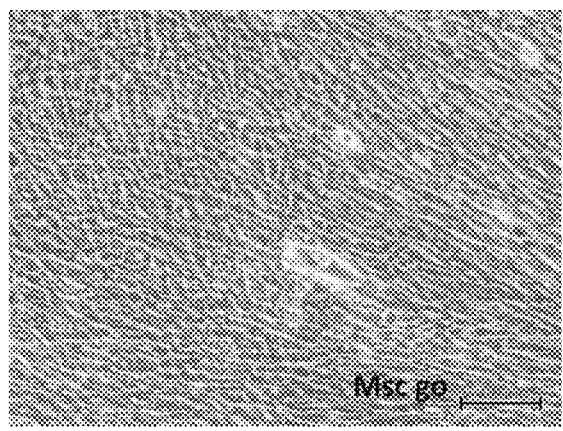
Figure 15:
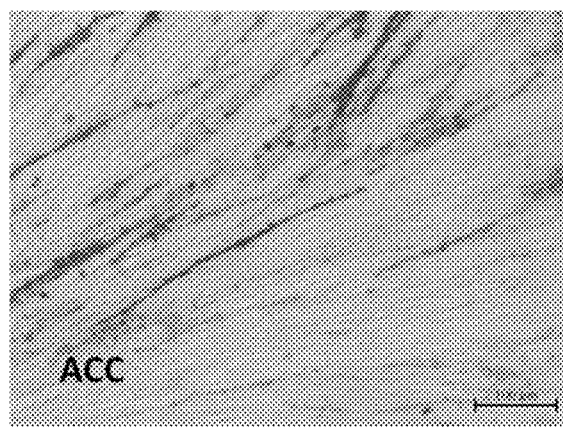
Figure 15:
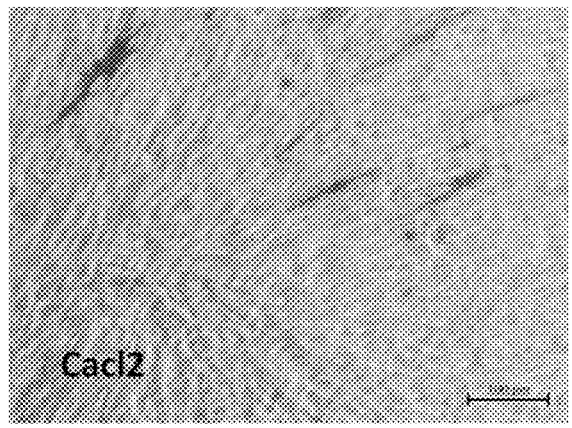
Figure 15:
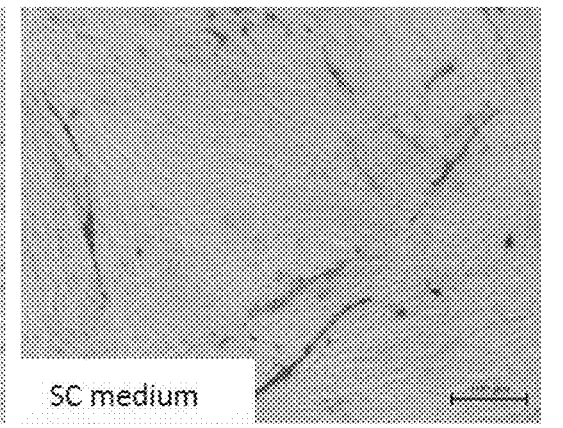

Alizarin staining of MDX cells treated with ACC enriched medium 10 days following seeding demonstrated no major differences in the staining among the treatments (see FIG. 15A-C). These results support that Alizarin Red staining of osteoblasts is due to calcium deposition by the osteoblast and not due to ACC deposition caused by the treatment itself (i.e. it is not an experimental artifact).

The staining of Alkaline phosphatase of MDX cell lines (FIG. 15D-F) demonstrated that there was no bone formation occurred. Interestingly, in Alkaline phosphatase stain enhanced myotubes formation was observed in ACC treated cells in comparison to cells grown in $CaCl_2$ supplemented medium or control.

CONCLUSIONS

Both independent staining, Alizarin Red and Alkaline phosphatase following the 10 days of seeding at different medium showed substantial stronger staining of the osteoblast cells deposition that were grown in medium supplemented with ACC in comparison to the controls used.

While large calcium deposition plaques were observed when cells were grown in the presence of ACC, such deposition was not observed for cells grown in a medium supplemented with $CaCl_2$. A stronger signal might indicate on a larger functionality, since the staining demonstrated more plaque deposition. The result obtained by the MDX cells staining suggests that the plaques are not originated from the ACC addition but are a direct result of the osteoblast functionally.

Example 23—ACC for Enhancement Sperm Motility

Materials and Methods

ACC Suspension Preparation 36 ml of 3% Calcium chloride solution was mixed with 4 ml of 0.3% Citric Acid solution and with 10 ml of 0.5% Triphosphate solution. Then 40 ml of 2% Sodium carbonate solution was added to precipitate ACC. 10 ml of the stabilizing solution containing 0.5% triphosphate was added to the ACC suspension creating stabilized ACC suspension. The elemental calcium concentration of the obtained suspension was 75 mM.

Sperm Collection

Sperm were collected 3 times from the same ram (exp. 1) or twice from 3 rams (exp. 2 & 3) and evaluated to concentration and motility at room temperature. The sperm was diluted to concentration of 50 million sperm/ml in Synthetic Oviduct fluid (SOF) comprising: 107.70 mM NaCl, 7.16 mM KCl, 1.19 mM KH2PO4, 1.71 mM CaCl2, 0.49 mM MgCl2, 25.07 mM NaHCO3, 3.30 mM Na lactate, and 1.50 mM glucose (10) in Milli-Q water. The osmolarity should be 270 mOsmol and the pH 7.55.

Sperm was then evaluated for motility using CASA (The riogenology, 2014, Volume 81, Issue 1, Pages 5-17) and cooled to 4° C. at 1° C./min.

Swim Up Procedure

Swim up procedure was performed at 38° C., the raw sperm (10 ul) was placed in eppendroph 1 ml vial and incubated for about 1 hour in SOF medium which was inserted in 0.25 ml straws (CBS, France). After 40-60 minutes the sperm which entered the straw were placed on a slide and evaluated by CASA.

Results

The motility of the freshly collected sperm was tested as described in materials and methods section with or without addition of amorphous calcium carbonate. The results are presented in Table 19.

TABLE 19

The motility assessment of sperm with and without the addition of ACC suspension 34 μl/ml (2.6 mM of elemental Ca).

|  | % motility | % progressive motility |
| --- | --- | --- |
| Control | 96 ± 1.15 | 55.3 ± 1.15 |
| ACC (34 μl/ml: 2.6 mM elemental Ca) | 95 ± 1 | 70.6 ± 3.2 |

It can be seen that sperm supplemented with ACC had much higher progressive motility than untreated sperm.

Example 24. Effect of ACC on Sperm Motility in a Swim Up Experiment

To evaluate the effect of ACC on sperm motility, a standard swim up experiment was performed in the presence of 17 μl/ml and 34 μl/ml of ACC suspension (1.3 and 2.6 mM of elemental Ca, respectively). The viable spermatozoa was counted after one hour and the results are summarized in Table 20.

TABLE 20

Effect of ACC on sperm motility in a swim up
experiment (concentration in million/ml)

| ACC concentration (elemental calcium concentration) | Sperm concentration (×10⁶/ml) | | |
|---|---|---|---|
| | exp 1 | exp 2 | exp 3 |
| control | 142 ± 7.3 | 97 ± 15 | 207 ± 12 |
| ACC 17 µl/ml (1.3 mM elemental Ca) | 523 ± 5.7 | 186 ± 14 | |
| ACC 34 µl/ml (2.6 mM elemental Ca) | | | 1463 ± 400 |

It can be clearly seen that addition of ACC significantly increased the number of viable spermatozoa in all experiments. In the samples supplemented with ACC, the number of viable spermatozoa was between 2 to 7 times higher than in the untreated samples.

Example 25. Effect of ACC Concentration on Sperm Motility in Swim-Up Experiment The effect of ACC concentration of the motility of sperm was tested by a swim-up experiment using 3 different samples for each ACC concentrations. The results are summarized in Table 21.

TABLE 21

Effect of ACC concentration on sperm motility
in swim up experiment (concentration in million/ml)

| ACC concentration (elemental calcium concentration) | Sperm concentration (×10⁶) |
|---|---|
| Control | 45.5 |
| ACC 8 µl/ml (0.6 mM elemental Ca) | 102, 77, 89 |
| ACC 17 µl/ml (1.3 mM elemental Ca) | 179, 170, 174 |
| ACC 34 µl/ml (2.6 mM elemental Ca) | 196, 200, 198 |
| ACC 60 µl/ml (4.6 mM elemental Ca)) | 182, 205, 193 |

It has been noted that the addition of 17 µl/ml ACC suspension to the synthetic oviduct fluid (SOF) solution and incubation at 38 C for 1 hour increased the concentration of motile sperm by at least 3 folds. Interestingly, higher concentration of ACC did not reduce the concentration of motile sperm after swim-up. It was concluded that ACC enhanced the concentration of sperm after swim-up procedure and did not have any bi-phasic effect for ionic calcium. Any ACC concentration above the minimum effective dose increases motility.

Example 26 ACC Preserves Ovaries In Vitro

Material and Methods

Ovaries were collected from mice (6 weeks old) cut to 0.4 mm×0.4 mm pieces. The ovaries were culture in 12 well plates. The culture medium was composed of: 90% Dulbecco's modified eagle medium-nutrient mixture F-12 (DMEM-F12) calcium depleted (medium without calcium ions, special preparation), 10% fetal bovine serum (FBS), 2 mM glutamine, 25 µg/mL gentamicin and 0.3-0.5% NVR-Gel with or without stabilized 3.4 mM ACC-PP. After 48 h of culturing, 5 IU of PMSG pregnant mare's serum gonadotrophin (PMSG) were added into the culture dish.

Results

Figure 16A:
FIGS. 16A-16B shows effect of stabilized ACC of in vitro cultured ovaries (A) in which granulosa cells surrounding the oocytes were intact versus control (B) (no ACC in the medium) in which non intact granulosa cells and oocyte at the Germinal Vesicles stage was observed.
Figure 16B:
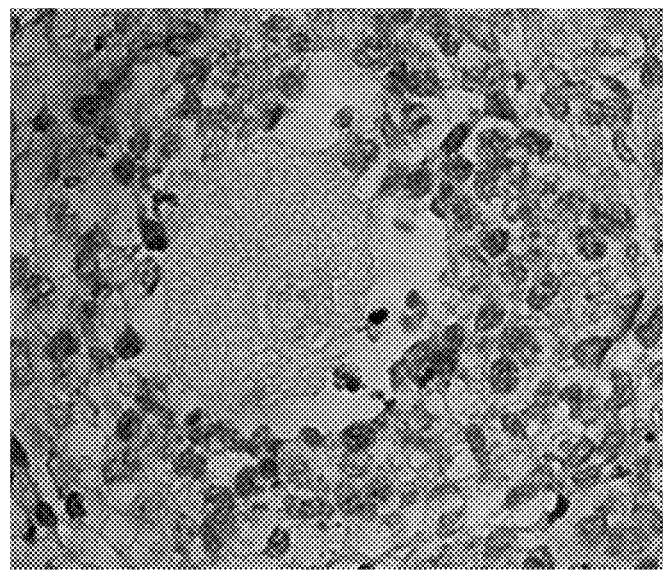

It can be seen on FIG. 16, that secondary follicles were developed after 2 weeks of in vitro culturing in the presence of stabilized ACC, and granulosa cells surrounding the oocytes were intact. On the contrary, secondary follicles in the control group show non-intact granulosa cells and Germinal vesicles oocyte. Much more follicles were observed in the ACC group, implying that addition of the ACC in the culture medium allows faster and better growth of follicles.

Although the present invention has been described herein above by way of preferred embodiments, thereof, it can be modified, without departing from the spirit and nature of the subject invention as defined in the appended claims.

The invention claimed is:

1. A method for in vitro fertilization, the method comprising:
 (a) in vitro fertilizing a mammalian oocyte; and
 (b) in vitro culturing the embryo(s);
 wherein step (a), step (b) or both steps (a) and (b) are performed in a cell culture medium including amorphous calcium carbonate (ACC) stabilized by at least one stabilizing agent.

2. The method of claim 1, further comprising in vitro culturing the embryo in a cell culture medium including ACC stabilized by at least one stabilizing agent, thereby enhancing embryo development.

3. The method of claim 1, further comprising a step of in vitro maturation of an oocyte in a cell culture medium including ACC stabilized by at least one stabilizing agent, prior to step (a).

4. The method of claim 1, wherein said at least one stabilizing agent is selected from the group consisting of a polyphosphate, phosphorylated amino acids, organic acids, phosphorylated, phosphonated, sulfated or sulfonated organic compounds, phosphoric or sulfuric esters of hydroxy carboxylic acids, bisphosphonate, saccharides and derivatives thereof, proteins, peptides, phosphorylated proteins, phosphorylated peptides, natural and synthetic biopolymers and derivatives thereof, and any combinations thereof, and/or an average diameter of the stabilized ACC primary particles is about 10 nm to about 500 nm.

5. The method of claim 1, wherein the at least one stabilizing agent is selected from the group consisting of phosphoserine, triphosphate, adenosine triphosphate, adenosine diphosphate, phytic acid, citric acid, etidronic acid, pyrophosphate, ethanol, hexamethaphosphate, chitin, and any combination thereof.

* * * * *